United States Patent
Slobitker et al.

(10) Patent No.: US 10,448,959 B2
(45) Date of Patent: Oct. 22, 2019

(54) BONE MATERIAL REMOVAL DEVICE AND A METHOD FOR USE THEREOF

(71) Applicant: T.A.G. Medical Devices—Agriculture Cooperative Ltd., Kibbutz Gaaton (IL)

(72) Inventors: Leon Slobitker, Carmiel (IL); Hagay Sitry, Kibbutz Gesher HaZiv (IL); Alexander Kotov, Kiryat-Ata (IL); Ran Weisman, Kfar-Vradim (IL)

(73) Assignee: T.A.G. Medical Devices—Agriculture Cooperative Ltd., Kibbutz Gaaton (IL)

( * ) Notice: Subject to any disclaimer, the term of this patent is extended or adjusted under 35 U.S.C. 154(b) by 0 days.

(21) Appl. No.: 15/318,677

(22) PCT Filed: Apr. 7, 2016

(86) PCT No.: PCT/IL2016/050370
§ 371 (c)(1),
(2) Date: Dec. 14, 2016

(87) PCT Pub. No.: WO2016/162869
PCT Pub. Date: Oct. 13, 2016

(65) Prior Publication Data
US 2017/0128086 A1    May 11, 2017

Related U.S. Application Data

(60) Provisional application No. 62/144,991, filed on Apr. 9, 2015, provisional application No. 62/151,375, filed on Apr. 22, 2015.

(51) Int. Cl.
*A61B 17/16* (2006.01)

(52) U.S. Cl.
CPC ...... *A61B 17/1675* (2013.01); *A61B 17/1617* (2013.01); *A61B 17/1631* (2013.01);
(Continued)

(58) Field of Classification Search
CPC .. A61B 17/16; A61B 17/1617; B23B 51/0045
(Continued)

(56) References Cited

U.S. PATENT DOCUMENTS

| | | | | | |
|---|---|---|---|---|---|
| 1,006,468 | A | * | 10/1911 | Des Isles | E04D 1/34 411/359 |
| 1,106,767 | A | * | 8/1914 | Young | E04D 1/34 411/359 |

(Continued)

FOREIGN PATENT DOCUMENTS

| | | |
|---|---|---|
| CN | 101677823 | 3/2010 |
| EP | 1535579 | 6/2005 |

(Continued)

OTHER PUBLICATIONS

Communication Relating to the Results of the Partial International Search dated May 19, 2016 From the International Searching Authority Re. Application No. PCT/IL2015/051033.
(Continued)

*Primary Examiner* — David W Bates

(57) ABSTRACT

A bone material removal device including a cannula, a bone drilling forward tip and a bore widening element including a bone carving portion that slides axially relative to the cannula and extends in a circumferential direction and wherein the axial movement of the bore widening element relative to the cannula brings a carving portions to travel and extend radially in a circumferential direction beyond a surface of the cannula and carve bone from a wall of a bore.

29 Claims, 25 Drawing Sheets

(52) U.S. Cl.
CPC ...... *A61B 17/1635* (2013.01); *A61B 17/1642* (2013.01); *A61B 17/1633* (2013.01)

(58) Field of Classification Search
USPC .......................................................... 411/359
See application file for complete search history.

(56) References Cited

U.S. PATENT DOCUMENTS

| | | | |
|---|---|---|---|
| 1,173,882 A * | 2/1916 | Smith | E04D 1/34 411/359 |
| 1,204,330 A * | 11/1916 | Adair | E04D 1/34 411/359 |
| 1,237,142 A * | 8/1917 | Aase | E04D 1/34 411/359 |
| 1,958,399 A | 5/1934 | Stephens | |
| 3,540,324 A | 11/1970 | Johansson | |
| 3,690,357 A | 9/1972 | Lugo | |
| 3,702,611 A | 11/1972 | Fishbein | |
| 3,945,076 A | 3/1976 | Sung | |
| 4,541,423 A | 9/1985 | Barber | |
| 4,635,737 A * | 1/1987 | Miyanaga | B23B 51/0045 175/284 |
| 4,710,070 A | 12/1987 | Alsen et al. | |
| 4,738,255 A * | 4/1988 | Goble | A61B 17/0401 29/243.519 |
| 4,992,010 A * | 2/1991 | Fischer | B23B 51/0045 175/286 |
| 4,998,981 A * | 3/1991 | Miyanaga | B23B 51/0045 175/202 |
| 5,507,606 A | 4/1996 | Steiner | |
| 5,645,589 A * | 7/1997 | Li | A61B 17/0401 411/24 |
| 5,681,320 A | 10/1997 | McGuire | |
| 5,817,095 A * | 10/1998 | Smith | A61B 17/1617 606/79 |
| 5,839,860 A | 11/1998 | Steiner | |
| 6,358,251 B1 | 3/2002 | Mirza | |
| 6,383,188 B2 | 5/2002 | Kuslich et al. | |
| 6,679,886 B2 | 1/2004 | Weikel et al. | |
| 6,746,451 B2 | 6/2004 | Middleton et al. | |
| 6,923,813 B2 | 8/2005 | Phillips et al. | |
| 7,097,648 B1 | 8/2006 | Globerman et al. | |
| 7,172,374 B2 | 2/2007 | Burr et al. | |
| 7,179,024 B2 | 2/2007 | Greenhalgh | |
| 7,637,910 B2 | 12/2009 | Schmieding et al. | |
| 7,682,378 B2 | 3/2010 | Truckai et al. | |
| 7,914,545 B2 | 3/2011 | Ek | |
| 7,938,835 B2 | 5/2011 | Boucher et al. | |
| RE42,757 E | 9/2011 | Kuslich et al. | |
| 8,038,679 B2 | 10/2011 | Wieland | |
| 8,048,079 B2 | 11/2011 | Iannarone | |
| 8,388,621 B2 | 3/2013 | Bourque et al. | |
| 9,381,021 B2 * | 7/2016 | Wagner | A61B 17/1615 |
| 9,950,445 B2 * | 4/2018 | Miyanaga | B28D 1/146 |
| 2002/0193799 A1 | 12/2002 | Chappuis et al. | |
| 2004/0126196 A1 | 7/2004 | Burr et al. | |
| 2004/0208717 A1* | 10/2004 | Greenhalgh | B23B 51/0018 408/224 |
| 2005/0113836 A1 | 5/2005 | Lozier et al. | |
| 2005/0131345 A1 | 6/2005 | Miller | |
| 2005/0240193 A1 | 10/2005 | Layne et al. | |
| 2006/0025774 A1 | 2/2006 | Fishbein et al. | |
| 2006/0149268 A1 | 7/2006 | Truckai et al. | |
| 2006/0195112 A1 | 8/2006 | Ek | |
| 2006/0241629 A1 | 10/2006 | Krebs et al. | |
| 2006/0264957 A1 | 11/2006 | Cragg et al. | |
| 2007/0123889 A1* | 5/2007 | Malandain | A61B 17/1617 606/79 |
| 2007/0276392 A1 | 11/2007 | Beyar et al. | |
| 2007/0282345 A1 | 12/2007 | Yedlicka et al. | |
| 2008/0114364 A1 | 5/2008 | Goldin et al. | |
| 2008/0183174 A1 | 7/2008 | Sikora et al. | |
| 2010/0168747 A1 | 7/2010 | Lynch et al. | |
| 2010/0249785 A1* | 9/2010 | Betts | A61B 17/1617 606/79 |
| 2011/0087257 A1 | 4/2011 | To et al. | |
| 2011/0098709 A1 | 4/2011 | Malandain et al. | |
| 2011/0164937 A1 | 7/2011 | Byrne et al. | |
| 2011/0166575 A1 | 7/2011 | Assell et al. | |
| 2011/0190832 A1 | 8/2011 | Taylor et al. | |
| 2011/0251616 A1 | 10/2011 | Osman et al. | |
| 2012/0022568 A1* | 1/2012 | Koblish | A61B 10/025 606/185 |
| 2012/0209274 A1 | 8/2012 | Belaney et al. | |
| 2012/0245585 A1 | 9/2012 | Kaiser et al. | |
| 2013/0165935 A1 | 6/2013 | Griffiths et al. | |
| 2014/0194880 A1 | 7/2014 | Schmieding et al. | |
| 2014/0257297 A1 | 9/2014 | Koogle, Jr. et al. | |
| 2014/0276844 A1 | 9/2014 | Bourque et al. | |
| 2014/0324052 A1 | 10/2014 | Carrison et al. | |
| 2015/0073417 A1* | 3/2015 | Norton | A61B 17/1617 606/80 |
| 2015/0265287 A1* | 9/2015 | Berberich | A61B 17/1615 606/80 |
| 2016/0038157 A1 | 2/2016 | Mirochinik et al. | |
| 2017/0224359 A1 | 8/2017 | Mirochinik et al. | |
| 2017/0245869 A1 | 8/2017 | Mirochinik et al. | |
| 2018/0360467 A1 | 12/2018 | Slobitker et al. | |

FOREIGN PATENT DOCUMENTS

| | | |
|---|---|---|
| EP | 1785103 | 5/2007 |
| ES | 2351563 | 2/2011 |
| JP | 2006-523542 | 10/2006 |
| JP | 2012-187384 | 10/2012 |
| WO | WO 01/58629 | 8/2001 |
| WO | WO 2010/065047 | 6/2010 |
| WO | WO 2010/115134 | 10/2010 |
| WO | WO 2013/192080 | 12/2013 |
| WO | WO 2014/089198 | 6/2014 |
| WO | WO 2014/174521 | 10/2014 |
| WO | WO 2016/063279 | 4/2016 |
| WO | WO 2016/162869 | 10/2016 |
| WO | WO 2017/137998 | 8/2017 |

OTHER PUBLICATIONS

International Preliminary Report on Patentability dated Nov. 5, 2015 From the International Bureau of WIPO Re. Application No. PCT/IL2014/050381.
International Search Report and the Written Opinion dated Aug. 4, 2016 From the International Searching Authority Re. Application No. PCT/IL2015/051033.
International Search Report and the Written Opinion dated Oct. 7, 2016 From the International Searching Authority Re. Application No. PCT/IL2016/050370.
International Search Report and the Written Opinion dated Sep. 10, 2014 From the International Searching Authority Re. Application No. PCT/IL2014/050381.
Invitation to Pay Additional Fees dated Aug. 1, 2016 From the International Searching Authority Re. Application No. PCT/IL2016/050370.
Official Action dated Nov. 2, 2016 From the US Patent and Trademark Office Re. U.S. Appl. No. 14/919,921.
Restriction Official Action dated Jul. 8, 2016 From the US Patent and Trademark Office Re. U.S. Appl. No. 14/919,921.
Restriction Official Action dated Feb. 11, 2016 From the US Patent and Trademark Office Re. U.S. Appl. No. 14/919,921.
International Preliminary Report on Patentability dated May 4, 2017 From the International Bureau of WIPO Re. Application No. PCT/IL2015/051033. (11 Pages).
Invitation to Pay Additional Fees dated May 17, 2017 From the International Searching Authority Re. Application No. PCT/IL2017/050170. (2 Pages).
Official Action dated Jul. 17, 2017 From the US Patent and Trademark Office Re. U.S. Appl. No. 15/498,731. (13 Pages).
Official Action dated Dec. 13, 2017 From the US Patent and Trademark Office Re. U.S. Appl. No. 15/498,731. (12 pages).

(56) References Cited

OTHER PUBLICATIONS

International Preliminary Report on Patentability dated Oct. 19, 2017 From the International Bureau of WIPO Re. Application No. PCT/IL2016/050370. (12 Pages).
International Search Report and the Written Opinion dated Aug. 11, 2017 From the International Searching Authority Re. Application No. IL2017/ 050170. (24 Pages).
Notification of Office Action and Search Report dated Aug. 15, 2017 From the State Intellectual Property Office of the People's Republic of China Re. Application No. 201480035299.2. (6 Pages).
Translation of Notification of Office Action dated Aug. 15, 2017 From the State Intellectual Property Office of the People's Republic of China Re. Application No. 201480035299.2. (3 Pages).
Advisory Action Before the Filing of an Appeal Brief dated Feb. 28, 2018 From the US Patent and Trademark Office Re. U.S. Appl. No. 15/498,731. (3 pages).
Communication Pursuant to Article 94(3) EPC dated Mar. 1, 2018 From the European Patent Office Re. Application No. 15804626.8. (3 Pages).
Notice of Reason for Rejection dated Feb. 27, 2018 From the Japan Patent Office Re. Application No. 2016-509605. (2 Pages).
Official Action dated Mar. 29, 2018From the US Patent and Trademark Office Re. U.S. Appl. No. 15/498,731. (15 pages).
Translation Dated Mar. 22, 2018 of Notice of Reason for Rejection dated Feb. 27, 2018 From the Japan Patent Office Re. Application No. 2016-509605. (2 Pages).
Applicant-Initiated Interview Summary dated Jul. 18, 2018 From the US Patent and Trademark Office Re. U.S. Appl. No. 15/498,731. (4 pages).
European Search Report dated Apr. 30, 2018 From the European Patent Office Re. Application No. 17205443.9. (5 Pages).
International Preliminary Report on Patentability dated Aug. 23, 2018 From the International Bureau of WIPO Re. Application No. PCT/IL2017/050170. (16 Pages).
Notice of Decision of Rejection dated Sep. 4, 2018 From the Japan Patent Office Re. Application No. 2016-509605. (4 Pages).
Translation Dated Oct. 5, 2018 of Notice of Decision of Rejection dated Sep. 4, 2018 From the Japan Patent Office Re. Application No. 2016-509605. (4 Pages).
Notification of Office Action dated Dec. 4, 2018 From the State Intellectual Property Office of the People's Republic of China Re. Application No. 201580069380.7 and Its Translation Into English. (4 Pages).
Supplementary European Search Report and the European Search Opinion dated Dec. 13, 2018 From the European Patent Office Re. Application No. 16776225.1. (8 Pages).
Supplementary European Search Report and the European Search Opinion dated Jan. 30, 2019 From the European Patent Office Re. Application No. 17749987.8. (6 Pages).

\* cited by examiner

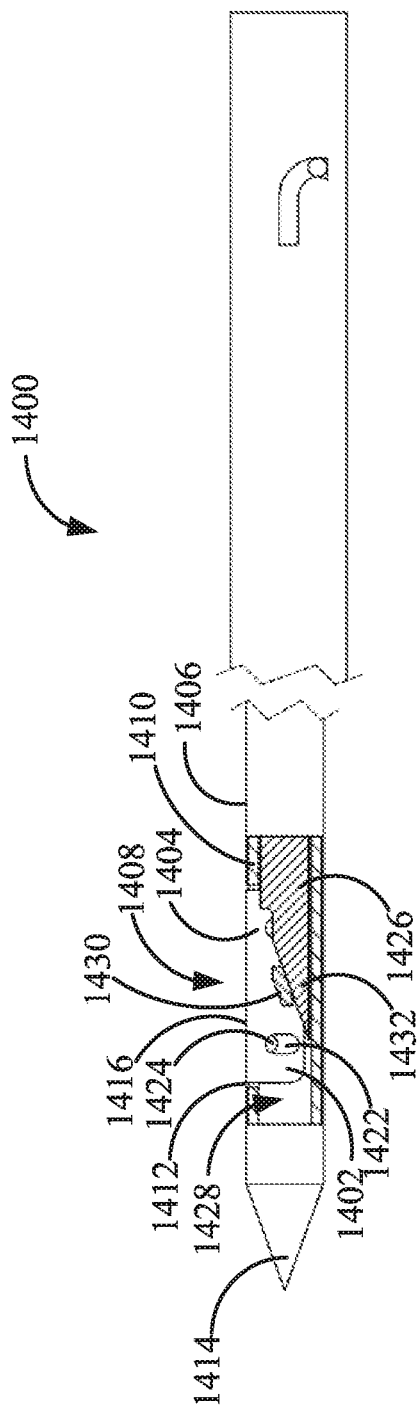
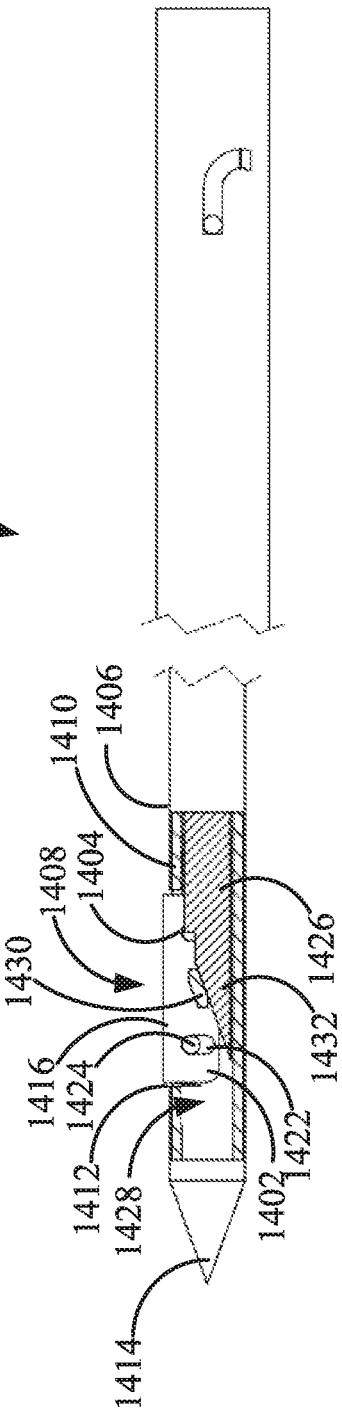

BONE MATERIAL REMOVAL DEVICE AND A METHOD FOR USE THEREOF

RELATED APPLICATIONS

This application is a National Phase of PCT Patent Application No. PCT/IL2016/050370 having International filing date of Apr. 7, 2016, which claims the benefit of priority under 35 USC § 119(e) of U.S. Provisional Patent Application Nos. 62/144,991 file on Apr. 9, 2015 and 62/151,375 file on Apr. 22, 2015. The contents of the above applications are all incorporated by reference as if fully set forth herein in their entirety.

FIELD OF THE INVENTION

The present invention, in some embodiments thereof, relates to bone removal devices, and more particularly, but not exclusively, to devices that change effective diameter of bores.

BACKGROUND OF THE INVENTION

Various orthopedic reconstructive procedures and particularly ligament or tendon reconstructive procedures such as, for example, Anterior Cruciate Ligament (ACL) reconstruction require, implantation of a surgical tissue graft (e.g., ligament graft) inserted into the bone in order to replace the injured tissue. The injured tissue is removed from the bone before the graft is inserted through a bore created by drilling.

Some ligament or tendon reconstructive procedures benefit from drilling an undercut deep to the surface of the bone to accommodate an anchor for the implanted tissue.

Some commonly used devices that produce an undercut in bone employ a blade having a single carving edge that circumferentially scrapes and widens a portion of a wall of a drilled bore.

Such techniques utilize high friction between the blade and bone not only requiring an effort to operate but may also produce debris mainly consisting of small particles that may interfere with anchor placement and removal of which may be challenging.

Various drilling tools employed to produce undercuts along bores drilled in bone rely on moveable components such as hinges, springs and similar to operate that may be expensive to manufacture and may tend to wear down and malfunction over time. Operation of such tools may also be somewhat cumbersome to handle and require several operational steps to function.

SUMMARY OF THE INVENTION

According to an aspect of some embodiments of the present invention there is provided a bone material removal device, comprising a forward tip, a cannula, a bore widening element including a bone carving portion, the element operative to axially slide relative to the cannula and at least partially extend in a circumferential direction and wherein axial movement of the bore widening element as a whole relative to said cannula radially extends said carving portion that travels and extends radially bringing the bore widening element from a closed retracted position in which the bone carving portion is retracted to within a diameter of the cannula or a virtual axial extension thereof to an open extended position in which the bone carving portion extends in a circumferential direction beyond a diameter of a surface of the cannula or virtual extension thereof and carves bone from a wall of a bore.

According to an aspect of some embodiments of the present invention there is provided at least one resilient arm including at least one carving portion at the end thereof; and wherein axial movement brings the at least one arm to engage a fixed surface that geometrically interferes with the axial movement and bends the arm deflecting the carving portions that travels and extends radially in a circumferential direction beyond a surface of the cannula and carves bone from a wall of a bore.

According to an aspect of some embodiments of the present invention there is provided a bone material removal device having a single elastic member bore widening element wherein the bore widening element includes at least two distally extending arms having at least one carving portion at a distal end thereof and separated by a longitudinal recess having a proximal closed end and a distal open end.

According to an aspect of some embodiments of the present invention there is provided a bone material removal device having a single elastic member bore widening element having one or more arms that define a widened portion at the distal end of the bore widening element that includes the carving portion and defines a distally facing inwardly proximally tapered surface at a distal aspect of the carving portion.

According to an aspect of some embodiments of the present invention there is provided a bone material removal device having a carving portion that includes at least one carving edge.

According to an aspect of some embodiments of the present invention there is provided a bone material removal device having a carving portion comprises at least two first and second carving edges angled in respect to each other and joined at least at one end.

According to an aspect of some embodiments of the present invention there is provided a bone material removal device having a first carving edge cuts a main portion of a fragment of bone creating a first surface of the fragment and the second carving edge cuts a second adjoining surface of the fragment detaching the fragment of bone.

According to an aspect of some embodiments of the present invention there is provided a bone material removal device having a bore widening element includes at least two distally extending arms having at least one carving portion at a distal end thereof and separated by a longitudinal recess and wherein the first carving edge, the second carving edge and the angle therebetween, define a rake angle that provides a surface up and along which removed residual material rises and is collected into the recess.

According to an aspect of some embodiments of the present invention there is provided a bone material removal device having a carving portion that also comprises a radially positioned curved plain bordered at one side thereof by the first carving edge and forming an end relief or clearance curve that prevents the rubbing of the carving portions against the bone.

According to an aspect of some embodiments of the present invention there is provided a bone material removal device having a carving portion that is joined with an outer surface of the arms by a generally proximally inwardly tapered surface.

According to an aspect of some embodiments of the present invention there is provided a bone material removal device having a protrusion.

According to an aspect of some embodiments of the present invention there is provided a bone material removal device wherein the axial movement of the bore widening element brings at least one resilient arm to engage the protrusion that geometrically interferes with the axial movement of the bore widening element and bends the arm deflecting the carving portions that travels and extends radially in a circumferential direction beyond a surface of the cannula and carves bone from a wall of a bore.

According to an aspect of some embodiments of the present invention there is provided a bone material removal device having a protrusion that extends proximally from a proximally facing surface between the forward tip and the bore widening element and wherein the at least one resilient arm also includes a distally facing inclined surface at a distal aspect of the carving portion thereof and wherein the axial movement brings the inclined surface of the carving portion to engage the protrusion that geometrically interferes with the axial movement of the bore widening element and bends the arm and deflects the carving portions radially.

It should be appreciated that in this and other embodiments, either of the two matching surfaces, or both, maybe inclined.

According to an aspect of some embodiments of the present invention there is provided a bone material removal device wherein the at least one resilient arm includes a centrally facing surface and wherein the protrusion abuts the centrally facing surface so that the axial movement of the bore widening element relative to the cannula brings the centrally facing surface to be urged against the protrusion that geometrically interferes with the axial movement of the arm, bends and deflects the arm bringing the carving portions to travel and extend radially beyond a surface of the cannula and carve bone from a wall of a bore.

According to an aspect of some embodiments of the present invention there is provided a bone material removal device wherein a resilient arm also comprises a non-carving portion that extends distally beyond at least one carving portion and bordered proximally thereby terminating at an inclined surface and wherein the axial movement brings the inclined surface of the non-carving portion to engage the protrusion that geometrically interferes with the axial movement of the bore widening element and bends the arm bringing the carving portions to travel and extend radially beyond a surface of the cannula and carve bone from a wall of a bore.

According to an aspect of some embodiments of the present invention there is provided a bone material removal device includes a carving portion that is extended radially by bending forces exerted on a single surface of at least one arm of the widening element.

According to an aspect of some embodiments of the present invention there is provided a bone material removal device wherein having a cannula that comprises a hollow portion and at least one through openings in a wall thereof and wherein the bone carving portion extends in a circumferential direction through at least one opening.

According to an aspect of some embodiments of the present invention there is provided a bone material removal device wherein a carving portions comprises at least one proximally inwardly tapered surface and the bore widening element is housed in a stressed state within the cannula and wherein the axial displacement urges the inclined surfaces against and over distally facing shoulders of at least one opening disengaging the inclined surfaces therefrom and bringing about radial extension of at least one carving portion.

According to an aspect of some embodiments of the present invention there is provided a bone material removal device wherein a radial extension of at least one carving portion is effected by the tendency of the stressed bore widening element to return to its original resting state.

According to an aspect of some embodiments of the present invention there is provided a bone material removal device wherein a bone material removal device also includes counter support to support the carving portion in the extended position.

According to an aspect of some embodiments of the present invention there is provided a bone material removal device wherein a bone material removal device also includes counter support to oppose centrally directed radial forces and prevent the carving portion from retraction back into the cannula.

According to an aspect of some embodiments of the present invention there is provided a bone material removal device wherein a bone material removal device also comprises a protrusion that acts as a counter support.

According to an aspect of some embodiments of the present invention there is provided a bone material removal device wherein the at least one arm, when fully deflected, is generally parallel to the longitudinal axis of the bone material removal device and the blade supported by a counter support.

According to an aspect of some embodiments of the present invention there is provided a bone material removal device, wherein a tip is a bone drilling tip.

According to an aspect of some embodiments of the present invention there is provided a method for removal of bone material from bone, comprising:

bringing a bore widening element having at least one resilient arm and at least one carving portion at the end thereof to move axially; and urging the resilient arm against a surface that geometrically interferes with the axial movement of the bore widening element and exerting a force on the arm in a radial direction; and bending the arm and radially deflecting the carving portions into an extended circumferential position; and carving bone from walls of a bore and creating an undercut in the bone.

According to an aspect of some embodiments of the present invention there is provided a method, wherein converting the axial force exerted against the surface by the axial movement of the bore widening element to a radially directed force radially deflecting the carving portions into an extended circumferential position.

According to an aspect of some embodiments of the present invention there is provided a method for removal of bone material from bone, comprising:

housing a bore widening element having at least one carving portion including at least one inclined surface in a stressed state within a cannula;

axially moving the bore widening element; and urging the inclined surfaces against and over shoulders of at least one opening in a wall of the cannula geometrically interfering with the axial movement of the bore widening element; and disengaging the surfaces from the shoulder; and allowing the bore widening element to return to a resting state by bringing the carving portions to travel and extend radially through the opening and beyond a surface of the cannula and carving bone from a wall of a bore.

According to an aspect of some embodiments of the present invention there is provided a method for removal of bone material from bone, comprising:

bringing a bore widening element having at least one resilient arm and at least one carving portion at the end thereof to move axially;

placing a geometrically interfering surface in the path of travel of the at least one resilient arm; and engaging the arm with the interfering surface bending and deflecting the arm; and bringing the carving portion to travel and extend radially; and carving bone from a wall of a bore.

According to an aspect of some embodiments of the present invention there is provided a bone material removal bone material removal device, comprising a cannula, and a single elastic member including a bore widening element having a carving portion and a forward tip and operative to axially slide relative to the cannula and to extend in a circumferential direction and wherein axial movement of the widening element relative to the cannula elastically radially extends the carving portion to an extended carving position.

According to an aspect of some embodiments of the present invention there is provided a bone material removal device, wherein a single elastic member is moveably housed in the cannula.

According to an aspect of some embodiments of the present invention there is provided a bone material removal device, wherein a forward tip is a bore drilling tip.

According to an aspect of some embodiments of the present invention there is provided a bone material removal device, wherein a carving portion is attached to at least one cylindrical portion.

According to an aspect of some embodiments of the present invention there is provided a bone material removal device, wherein a single elastic member is movingly housed in the cannula.

According to an aspect of some embodiments of the present invention there is provided a bone material removal device, wherein a cannula has a proximal portion having an inner circumference substantially larger than the outer diameter of the thickest portion of the single member.

According to an aspect of some embodiments of the present invention there is provided a bone material removal device, wherein a cannula also includes an inwardly tapered portion located adjacent to a distal end of the cannula and a cylindrical portion.

According to an aspect of some embodiments of the present invention there is provided a bone material removal device, wherein a diameter of a inner circumference of the cylindrical portion located at the distal end of the cannula is substantially equal to the outer diameter of the thickest portion of the single member and supports primarily axial and rotational movement and minimal to no radial movement of the single elastic member.

According to an aspect of some embodiments of the present invention there is provided a bone material removal device, wherein in operation, a drilling tip acts as a first shaft capture point and a point of contact between the bone widening element and an inner circumference of the cannula acts as a second shaft capture point.

According to an aspect of some embodiments of the present invention there is provided a bone material removal device, wherein axial movement of an elastic member in respect to a cannula shortens the distance between a first shaft capture point and the second shaft capture point, increasing the rigidity of a bone widening element and bringing the carving portion to be translated radially.

According to an aspect of some embodiments of the present invention there is provided a bone material removal device, wherein contact of an elastic member with a tip of a cannula creates a third shaft capture being at or below a threshold length from the first shaft capture at which the distal end of the bore widening element loses its resilience, becomes rigid bringing the carving portion to be translated radially.

According to an aspect of some embodiments of the present invention there is provided a bone material removal device, wherein in a cannula an elastic member is in a stressed state in which the first and second cylindrical portions are not aligned with a longitudinal axis of the bone material removal device.

According to an aspect of some embodiments of the present invention there is provided a bone material removal device, wherein resilience of an elastic member supports accommodation of the widening element within a bore drilled by a bore drilling tip conforming to the diameter thereof.

According to an aspect of some embodiments of the present invention there is provided a bone material removal device, wherein at least a peak of the carving portion does not protrude radially and remains generally aligned with the longitudinal axis of the bone material removal device.

According to an aspect of some embodiments of the present invention there is provided a bone material removal device, wherein a carving portion comprises at least one carving edge.

According to an aspect of some embodiments of the present invention there is provided a bone material removal device, wherein a carving portion comprises at least two first and second carving edges angled in respect to each other and joined at least at one end.

According to an aspect of some embodiments of the present invention there is provided a bone material removal device, wherein the first carving edge cuts a main portion of a fragment of bone creating a first surface of the fragment and the second carving edge cuts a second adjoining surface of the fragment detaching the fragment of bone.

According to an aspect of some embodiments of the present invention there is provided a bone material removal device, wherein bore widening element includes at least two distally extending arms having at least one carving portion at a distal end thereof and separated by a longitudinal recess and wherein the first carving edge, the second carving edge and the angle therebetween, define a rake angle that provides a surface up and along which removed residual material rises and is collected into the recess.

According to an aspect of some embodiments of the present invention there is provided a bone material removal device, wherein a carving portion comprises a radially positioned curved plain bordered at one side thereof by the first carving edge and forming an end relief or clearance curve that prevents the rubbing of the carving portions against the bone.

According to an aspect of some embodiments of the present invention there is provided a method for removal of bone material from bone, comprising drilling a bore in the bone, introducing a single elastic member including a bore widening element having a carving portion and a tip through a cannula into the bore and stressing the member to conform to the diameter of the bore, reducing the distance between a shaft capture point on the member and the tip bringing about a reduction of a bending moment acting upon the carving portion and increasing the rigidity of the member, bringing about radially directed force on the carving portion urging it to extend radially to an extended position and carving bone from walls of a bore and creating an undercut in the bone.

According to an aspect of some embodiments of the present invention there is provided a method for removal of bone material from bone, comprising drilling a bore in the bone, introducing a single elastic member including a bore widening element having a carving portion and a tip through a cannula into the bore stressing the member to conform to the diameter of the bore, reducing the distance between a shaft capture point on the member and the tip relieving the stress on the member, allowing the member to return to a resting state bringing about radially directed force on the carving portion urging it to extend radially to an extended position and carving bone from walls of a bore and creating an undercut in the bone.

According to an aspect of some embodiments of the present invention there is provided a bone material removal device, comprising a forward tip, a cannula, a widening element including a bone carving portion operative to axially slide relative to the cannula and move between a resting state and a stressed state and to extend in a circumferential direction; and
wherein axial movement of the widening element relative to the cannula elastically radially extends the blade to an extended carving position.

According to an aspect of some embodiments of the present invention there is provided a bone material removal device, comprising a cannula, a bore widening element including at least one bone carving portion and an inclined surface, a pusher rod and wherein the bore widening element is limited to movement in a radial direction only and wherein the pusher rod moves axially, engages the inclined surface actuating the bore widening element that travels in a purely radial direction, bringing the carving portion to travel and extend radially beyond a surface of the bone material removal device.

According to an aspect of some embodiments of the present invention there is provided a bone material removal device, wherein movement of a bore widening element is limited by a radial-direction-guiding mechanism.

According to an aspect of some embodiments of the present invention there is provided a bone material removal device, wherein a radial-direction-guiding mechanism comprises elongated slot-like cutouts cut through the width of the bore widening element, the length of the cutouts oriented radially from the longitudinal axis of the bone material removal device and at least one pin fixed to a wall of the device and protruding radially inward through the cutouts.

According to an aspect of some embodiments of the present invention there is provided a bone material removal device, wherein a bore widening element is resiliently attached to a wall of the device by a resilient attachment that exerts tension, optionally constant, in a radially inward direction According to an aspect of some embodiments of the present invention there is provided a bone material removal device, wherein a resilient attachment resists outward radial extension of the bore widening element.

According to an aspect of some embodiments of the present invention there is provided a bone material removal device, wherein comprising a forward tip and at least one opening located at a predetermined distance proximally from a forward tip.

According to an aspect of some embodiments of the present invention there is provided a bone material removal device, wherein a forward tip is a bone drilling tip.

According to an aspect of some embodiments of the present invention there is provided a bone material removal device, wherein a bone material removal device also includes a lumen that communicates with the atmosphere via the opening, and wherein at rest the bone carving portion is at least partially retracted into the lumen, disposed within margins of opening and not protruding therefrom.

According to an aspect of some embodiments of the present invention there is provided a bone material removal device, wherein a tip of the pusher rod is inclined.

According to an aspect of some embodiments of the present invention there is provided a bone material removal device, wherein a carving portion comprises at least one carving edge.

According to an aspect of some embodiments of the present invention there is provided a bone material removal device, wherein a carving portion also comprises a radially positioned curved surface bordered at one side thereof by the first carving edge and forming an end relief or clearance curve that prevents the rubbing of the carving portions against the bone.

According to an aspect of some embodiments of the present invention there is provided a bone material removal device, wherein the carving portion comprises at least two first and second carving edges angled in respect to each other and joined at least at one end.

According to an aspect of some embodiments of the present invention there is provided a bone material removal device, wherein a first carving edge cuts a main portion of a fragment of bone creating a first surface of the fragment and the second carving edge cuts a second adjoining surface of the fragment detaching the fragment of bone.

According to an aspect of some embodiments of the present invention there is provided a bone material removal device, wherein a bore widening element includes at least two distally extending arms having at least one carving portion at a distal end thereof and separated by a longitudinal recess and wherein the first carving edge, the second carving edge and the angle therebetween, define a rake angle that provides a surface up and along a clearance curve which removed residual material rises and is collected into the device.

According to an aspect of some embodiments of the present invention there is provided a method for removal of bone material from bone from bone, comprising:
  limiting movement of a bore widening element having a carving portion and an inclined surface to movement in a radial direction only, axially moving a pusher rod,
  engaging the pusher rod with the inclined surface, actuating the bore widening element that travels in a purely radial direction, bringing the carving portion to travel and extend radially beyond a surface of a bone material removal device; and carving a portion of bone.

According to an aspect of some embodiments of the present invention there is provided a method wherein axially moving a pusher rod through a lumen of a cannula.

According to an aspect of some embodiments of the present invention there is provided a method, wherein radially extending a carving portion through an opening in a wall of the cannula.

According to an aspect of some embodiments of the present invention there is provided a method, wherein radially extending a carving portion against radially inward tension effected by a resilient attachment of the bore widening element to a wall of the cannula.

The present invention, in some embodiments thereof, seeks to provide an improved bone material removal device.

There is thus provided in accordance with an embodiment of the present invention a bone material removal device, including a cylindrical element arranged along a longitudinal axis and having a proximal end and a distal end, the distal end has a first cylindrical portion, a second cylindrical portion and a radially extending protrusion which joins the first cylindrical portion and the second cylindrical portion and extends radially outwardly from the longitudinal axis.

Preferably, the protrusion extends outwardly from the longitudinal axis by 0.1 mm-0.2 mm.

In accordance with an embodiment of the present invention, the drilling device including a cannula having a proximal cylindrical portion of a first diameter and a distal cylindrical portion of a second diameter, the first diameter is substantially greater than the second diameter, a bone material removal device adapted to be inserted and longitudinally displaced with respect to the cannula and having a cylindrical element, the diameter of the cylindrical element substantially equals the second diameter.

In accordance with an embodiment of the present invention, a method of drilling a varying diameter bore, including the steps of:

providing a cannula; providing a cylindrical element arranged along a longitudinal axis and having a proximal end and a distal end and adapted to be inserted and longitudinally displaced with respect to the cannula; the distal end has a radially extending protrusion which extends outwardly from the longitudinal axis; distally advancing the cylindrical element with respect to the cannula to create a longitudinal bore within a bone of a patient; further distally advancing the cylindrical element with respect to the cannula to create an undercut using the radially extending protrusion.

In accordance with an embodiment of the present invention, a bone material removal device configured to be advanced in two stages, including a cylindrical element arranged along a longitudinal axis and having a proximal end and a distal end, the distal end has a first cylindrical portion, a second cylindrical portion and a radially extending protrusion which joins the first cylindrical portion and the second cylindrical portion and extends outwardly from the longitudinal axis. A first stage in which the radially extending protrusion is deflected and the first cylindrical portion, the second cylindrical portion and the radially extending protrusion are aligned along the longitudinal axis to create a straight bore within a bone; and a second stage in which the radially extending protrusion radially protrudes from the longitudinal axis to create an undercut within the bone.

In accordance with another embodiment of the present invention, a bone material removal device, including a drilling element having an outer surface and a widening element arranged along a mutual longitudinal axis, and wherein the drilling element and the widening element are longitudinally displaceable with respect to each other, the widening element selectively assumes a closed position enabling drilling of a first bore of a first diameter and an open position enabling drilling of a second bore of a second diameter, whereas the second diameter is preferably greater than the first diameter.

Preferably, the widening element includes cutting edges and in the closed position, the cutting edges extend radially to be aligned with the outer surface of the drilling element.

Further preferably, in the open position, the cutting edges extend radially outwardly from the outer surface of the drilling element to form an undercut within the bone of a patient.

Still further preferably, the length of the undercut is a function of the length of the cutting edge.

In accordance with an embodiment of the present invention, the drilling element further has an internal protrusion and the widening element further has deflectable arms spaced one from another and having at least one widened portion defining the cutting edge. The bone material removal device assumes the open position when the deflectable arms slide over the internal protrusion and thus are spaced further away from each other.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 14A and 14B are cross section view simplified illustrations of additional embodiments of a bone material removal device.

DESCRIPTION OF EMBODIMENTS OF THE INVENTION

Figure 1:
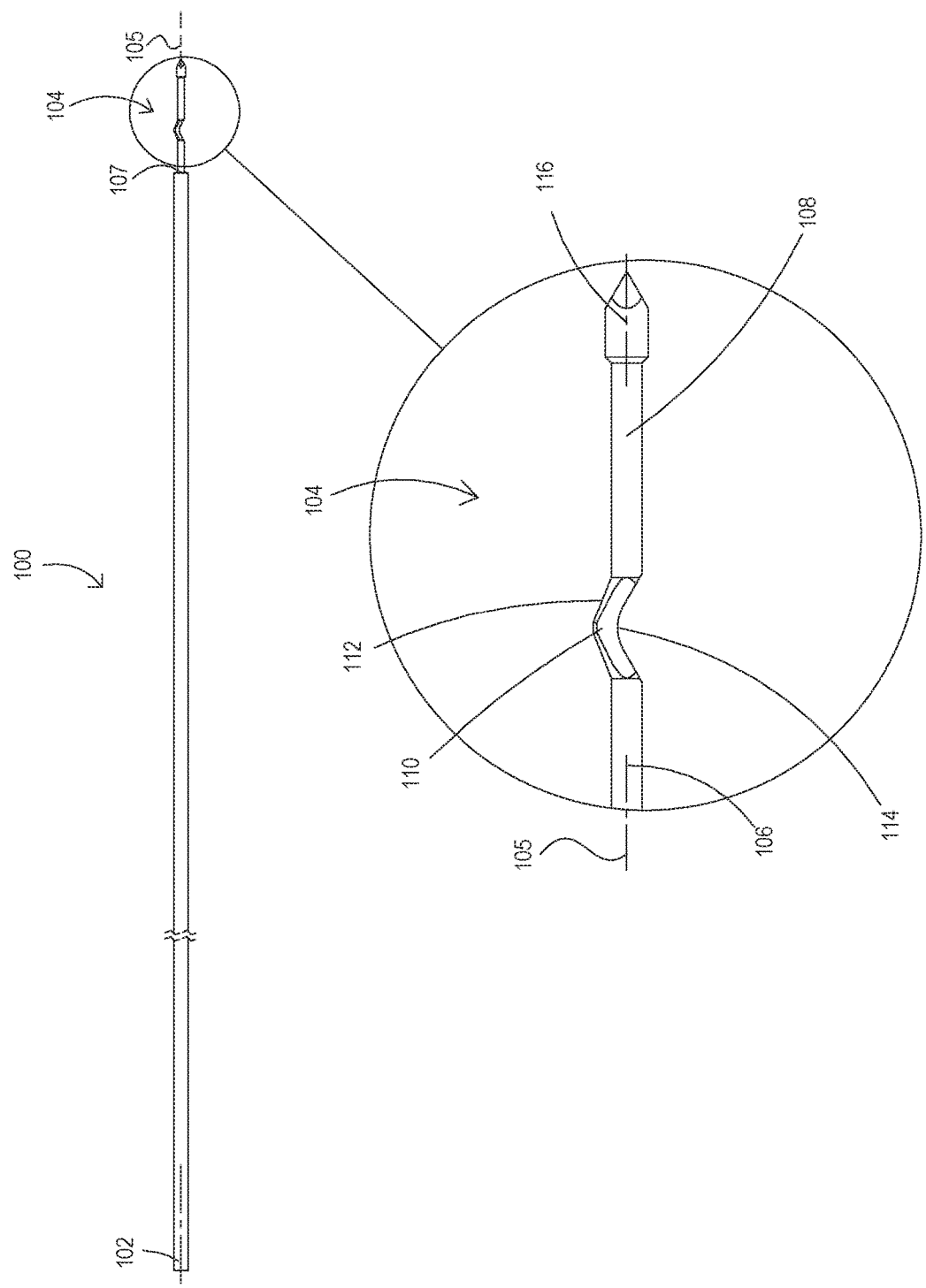
FIG. 1 is a simplified side view illustration and an enlargement view of a bone material removal device constructed and operative in accordance with an embodiment of the present invention, shown in an unstressed orientation and outside of a bone of a patient.

The term "bone material removal device" as used in this disclosure should be taken to mean a device that separates a portion of bone material in any form from a bone regardless of whether the separated material is cleared away from the bone or not.

The term "carving edge" as used in this disclosure should be taken to mean an edge of a portion of the bone material removal device operative to separate a portion of bone material, in any form, from a bone.

The term "carving portion" as used in this disclosure should be taken to mean a portion of the bone material removal device including a carving edge.

The term "shaft capture" and "shaft capture point" are used interchangeably in this disclosure and mean a point of contact between a shaft and a surrounding surface that temporarily limits radial movement of the shaft at that location.

A bone material removal device is disclosed herein, which is particularly useful for drilling a small diameter bore having one or more portions with varying diameters.

An aspect of some embodiments of the invention relates to a bone material removal device in which axial movement of at least a portion of the device is converted to radial extension of one or more carving portions. In some exemplary embodiments of the invention, the conversion is without constraining axial movement of a part of the removal device. Optionally or alternatively, the conversion is by geometrical interference with axial movement, which interference converts axial movement into radial extension, while optionally allowing axial movement past the interference, so there is no constraint. In some exemplary embodiments of the invention, the entire bone removal device is a single monolithic element formed of one piece of material, for example, metal. In some exemplary embodiments of the invention, the bone removal device is in two or more parts, one which moves axially and one which moves radially.

In some exemplary embodiments of the invention, radial movement extends said carving portion from a reduced diameter which is smaller than (or larger by no more than 10% or 20 or intermediate percentages) a bore in the bone and/or diameter of enclosing cannula or a virtual axial extension of the cannula in a distal direction, to an expanded diameter which extends radially beyond a surface of the cannula and/or a surface of said virtual extension, for example, extending 10%, 20%, 30%, 40%, 50% or intermediate or greater percentages of a radius of the cannula or virtual axial extension thereof and/or bore (e.g., typical diameter without widened section).

In some exemplary embodiments of the invention, the bone removal device comprises a carving portion, which portion translates to a new radial position. In some exemplary embodiments of the invention, the portion does not pivot and/or otherwise rotate around an axial hinge. It is a particular feature of some embodiments of the invention that the carving portion is robust. Optionally, the carving portion has cross-section of, for example, at least 20%, 40%, 60%, 70% or intermediate or greater percentages of a cross-section of a lumen of a cannula within which said portion is located. Optionally or alternatively, the portion is robust and does not bend during deployment, rather, any bending is at a part of the device which is not part of the carving portion. In some exemplary embodiments of the invention, robustness is provided by said portion material extending in a pure radial direction from inside the cannula, which it is optionally supported by the cannula to outside the cannula where it cute. Optionally, such extension is provided over at least 50%, 60%, 80% or greater or intermediate percentages of the axial length of the carving edge of the carving portion.

In some exemplary embodiments of the invention, translation is relatively or substantially pure radial translation, for example, including less that 75%, 60%, 30%, 20%, 10% or smaller or intermediate percentages of axial translation, as a percentage of distance of radial translation.

In some exemplary embodiments of the invention, radial movement comprises a bending of the bone removal device, but not at a carving edge and/or not at a bending of more than 10, 20, 30, 40 or 50 degrees or intermediate angles. Optionally or alternatively, any bending is at a bending radius of more than 1 mm, 3 mm, 5 mm, 10 mm or intermediate or greater bending radiuses.

In some exemplary embodiments of the invention, any bending is due to radially applied forces on the carving portion rather than axially applied forces.

An aspect of some embodiments of the invention relates to a method in which converting axial force exerted against a surface by axial movement of a bore widening element to a radially directed force radially deflecting the carving portions into an extended circumferential position.

An aspect of some embodiments of the invention relates to an elastic bone material removal device being a single member that may be moveably housed in a cannula. The bone material removal device may include a bore drilling tip and a bore widening element being a protrusion including a carving portion, disposed between two cylindrical portions. In operation, the drilling tip may act as a first shaft capture and a point of contact between the bore widening element and an inner circumference of the cannula may act as a second shaft capture. Axial movement of the device in respect to the cannula changes the location of the second shaft capture and shortens the distance between the first and second shaft captures, increasing the rigidity of the bore widening element. Further axial movement brings the bore widening element in contact with the tip of the cannula and creates a third shaft capture being at the shortest distance from the first shaft capture (the bore drilling tip) in respect to the distance of the second shaft capture from the drilling tip. The distance between the third and first shaft captures being below the bore widening element distal end threshold length at and below which the distal end of the bore widening element loses its resilience, becomes rigid bringing the carving portion to be translated radially to perform, for example, an undercut.

An aspect of embodiments of the invention relates to an elastic bone material removal device bone including a widening element with one or more resilient arms including carving portions at an end thereof and urged to move axially and engage a fixed surface that bends the arms and deflects the carving portions radially. Alternately and optionally, the bore widening element includes one or more arms having carving portions may be fixed in place and a moveable surface may be urged to move axially to engage the bore widening element, bend the arms and deflect the carving surface radially.

An aspect of embodiments of the invention relates to a bore widening element including one or more carving portions that may be limited to movement in a radial direction only and a pusher rod that moves axially to engage the bore widening element actuating the bore widening element that travels in a purely radial direction and bringing a carving portion thereof to travel and extend radially beyond a surface of a bone material removal device.

An aspect of embodiments of the invention relates to an elastic bone material removal device with bore widening element that includes one or more carving portions having proximally inwardly tapered or inclined surfaces and may be housed in a stressed state within a cannula. Axial displacement of the bore widening element along the cannula may bring the proximally inwardly tapered or inclined surfaces to be urged against and slide over shoulders of openings in the cannula wall and eventually be disengaged from the shoulders, allowing for gradual radial extension of one or more carving edges through the opening effected by the tendency of the bore widening element to return to its original resting state.

An aspect of embodiments of the invention relates to a bone material removal device including a moveable bore widening element being a single elastic member having a carving portion and in which axial movement of the bore widening element in respect to a fixed deflecting surface brings a non-carving end-portion of the bore widening element to contact the fixed surface and be deflected thereby bringing the carving portions to travel and extend radially beyond a surface of the cannula and carve bone from a wall of a bore. Alternately and optionally, the bore widening element may fixed and the deflecting surface moveable to be axially moved to engage the fixed bore widening element, bend the arms and deflect the carving portion radially.

Additionally and optionally, some embodiments of the invention relate to a bone material removal device including a hingeless mechanism operative to effect transition of the device from a resting state to a stressed state and vice versa and convert axial movement relative to a cannula of a bore widening element having one or more carving edges to radial movement and extension of the carving edges.

Additionally and optionally some embodiments of the invention relate to a bone material removal device accommodated within a cannula and includes a mechanism operative to collect and remove residual material and debris such as bone fragments from a created undercut and store the debris within the cannula.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a simplified side view illustration and an enlargement thereof of a bone material removal device constructed and operative in accordance with an embodiment of the present invention, shown in an unstressed or resting state and outside of a bone of a patient.

FIG. 1 illustrates a bone material removal device 100 that may be a single elastic member that includes both a bore drilling tip 116 and a radially protruding circumferentially bore widening element 110 having a carving portion. Bone material removal device 100 may have a proximal end 102 and a distal end 104. Device 100 may be mainly arranged along a longitudinal axis 105 and may be formed from a biocompatible shape memory alloy such as, for example, Nitinol.

As shown in the example of FIG. 1 bone material removal device 100 may optionally be formed as a cylinder at the majority of its longitudinal extent. The cylinder optionally may have a diameter in the range of 0.5 mm-3 mm, alternatively and optionally in the range of 0.5 mm-2.5 mm and alternatively and optionally in the range of 1 mm-2 mm.

It is a particular feature of an embodiment of the present invention that distal end 104 of bone material removal device 100 may optionally have a first generally cylindrical portion 106 terminating at a distally facing shoulder 107, a second generally cylindrical portion 108 and a bore widening element slightly radially extending so that the bore widening element does not depart from the diameter of a bore drilled by bore drilling tip 116. In some embodiments the bore widening element may extend radially with respect to longitudinal axis 105 for example in a conical shape, arc shape, triangular shape or any other shape.

In the embodiment of FIG. 1, the bore widening element is a slightly radially extending eccentric protrusion 110 having a generally convex outer surface 112 including a carving portion throughout its length and a generally concave inner surface 114. In other embodiments inner surface 114 may have other geometrical shapes. E.g., inner surface 114 may be flat forming a triangular protrusion 110. Protrusion 110 optionally joins first cylindrical portion 106 and second cylindrical portion 108. In the unstressed position of the embodiment depicted in FIG. 1, protrusion 110 may optionally extend outwardly from longitudinal axis 105 by 0.05-0.4 mm, alternatively and optionally by 0.075-0.3 mm and alternatively and optionally by 0.1 mm-0.2 mm.

In the embodiment of FIG. 1, it is noted that the outer diameter of distal end 104 of the bone material removal device 100 is smaller than the outer diameter of the remainder of the bone material removal device 100.

In the unstressed position of the embodiment depicted in FIG. 1, the majority of the longitudinal extent of bone material removal device 100 is arranged along longitudinal axis 105 except for protrusion 110 that may extend radially outwardly therefrom.

Bone material removal device 100 bore drilling tip 116 at the distal end 104 thereof, may be located distally from second cylindrical portion 108.

It is noted that the length of the distal end 104 is optionally more than a threshold length of, for example, 10 mm in order to prevent rigidity thereof. As will be explained in greater detail below, this characteristic allows to vary the rigidity of distal end 104 as desired by lengthening or shortening the distance between bore drilling tip 116 and a shaft capture point located along device 100. In other words, the shorter the length between bore drilling tip 116 and a shaft capture point located along device 100 the greater the rigidity of distal end 104 down to a threshold length (e.g., 8 mm) at and below which distal end 104 becomes fully rigid.

The length of distal end 104 may optionally be in the range of 10 mm-25 mm, alternatively and optionally 13 mm-23 mm and alternatively and optionally 15 mm-20 mm.

It is appreciated that in the unstressed or resting state of bone material removal device 100 seen in FIG. 1, first cylindrical portion 106 and second cylindrical portion 108 are mutually aligned along longitudinal axis 105.

Figure 2:
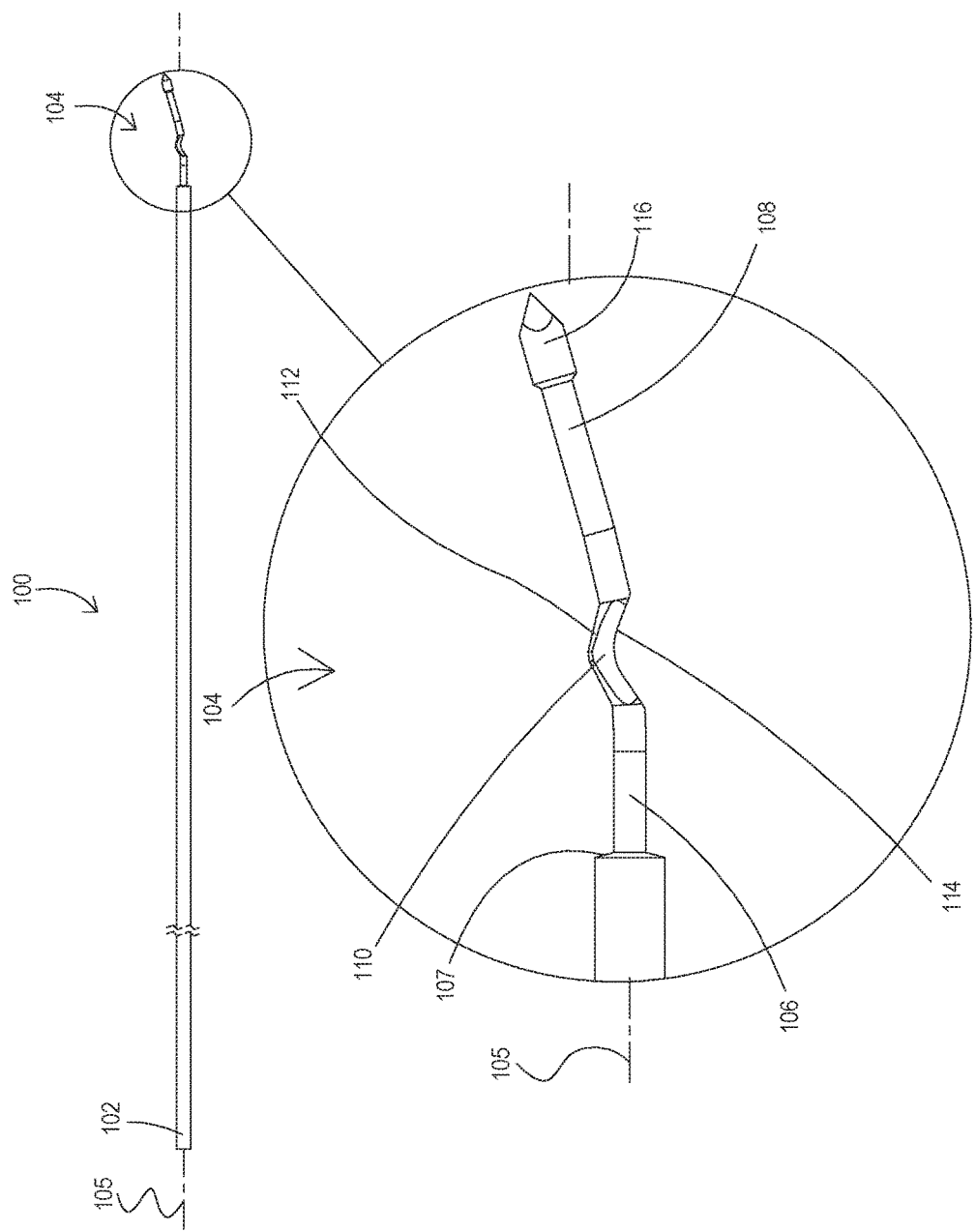
FIG. 2 is a side view illustration and an enlargement view of a bone material removal device of FIG. 1 shown in a deflected orientation and outside of a bone of a patient.

Reference is now made to FIG. 2, which is a side view illustration and an enlargement view of the bone material removal device embodiment of bone material removal device 100 of FIG. 1 in a stressed state. The example shown in FIG. 2 demonstrates the elastic qualities of bone material removal device 100 derived from material characteristics e.g., those of shape memory alloys. As shown in FIG. 2, when stressed, bone material removal device 100 shown outside a bone of a patient can be elastically deformed into a deflected orientation. However, due to its elastic and shape memory qualities, bone material removal device 100 may return to its original unstressed or resting state shape shown in FIG. 1 once stress is relieved therefrom.

In the example seen in FIG. 2, distal end 104 of the bone material removal device 100 is radially deflected due to the elastic characteristics of the bone material removal device 100. First cylindrical portion 106 and second cylindrical portion 108 are not aligned with longitudinal axis 105. The resilience of distal end 104 of the elastic member being bone material removal device 100 at this stage also supports accommodation of distal end 104 within a bore drilled by bore drilling tip 116 conforming to the diameter thereof, at least the peak if not all of the carving portion of convex outer surface 112 does not protrude radially and remains generally aligned with longitudinal axis 105.

Figure 3:
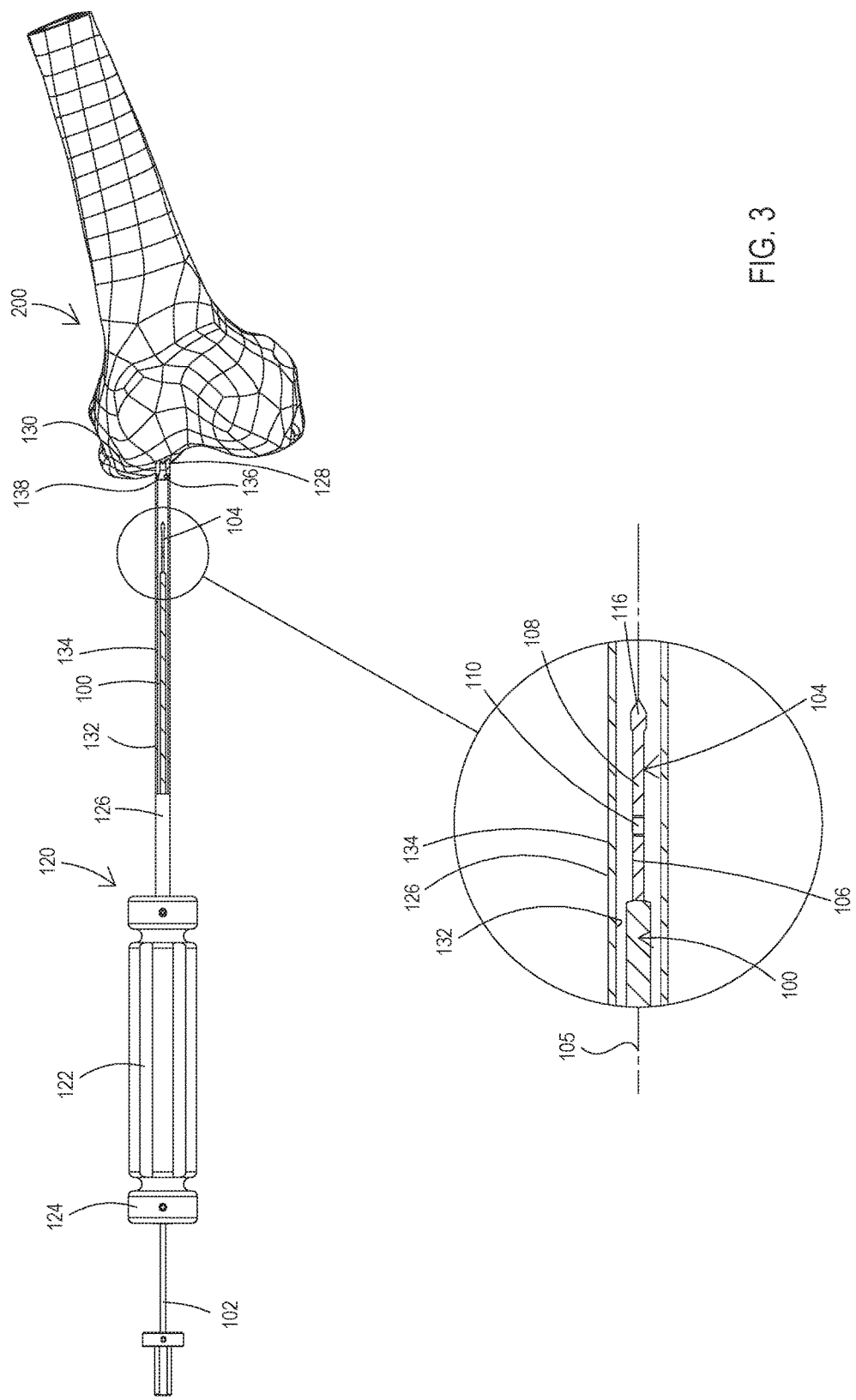
FIG. 3 is a partial cut away side view illustration and an enlargement view of a bone material removal device of FIG. 1 inserted into a cannula, showing the positioning of the cannula over the bone of a patient.

Reference is now made to FIG. 3, which is a partial cut away side view illustration and an enlargement view of the bone material removal device 100 of FIG. 1 inserted into a cannula, showing the positioning of the cannula over the bone of a patient.

The embodiment of the bone material removal device of FIG. 3 depicts one example of bone material removal device 100 inserted into a drill guiding tool 120 having a handle 122 at its proximal end 124 and a longitudinal cannula 126 at its distal end 128, tool 120 is arranged along longitudinal axis 105. Cannula 126 has a teethed tip 130 at its distal end for fixedly positioning the cannula over a location on a patient's bone 200. Drill guiding tool 120 may be positioned over the patient's bone 200 such that teethed tip 130 of cannula 126 engages the bone 200 and the bone material removal device 100 inserted into cannula 126, extend along proximal cylindrical portion 134 and terminate proximally to the inwardly tapered portion 136. In the example of FIG. 3 bone material removal device 100 is shown to be positioned in the unstressed or resting state similar to that shown in FIG. 1.

Figure 4A:
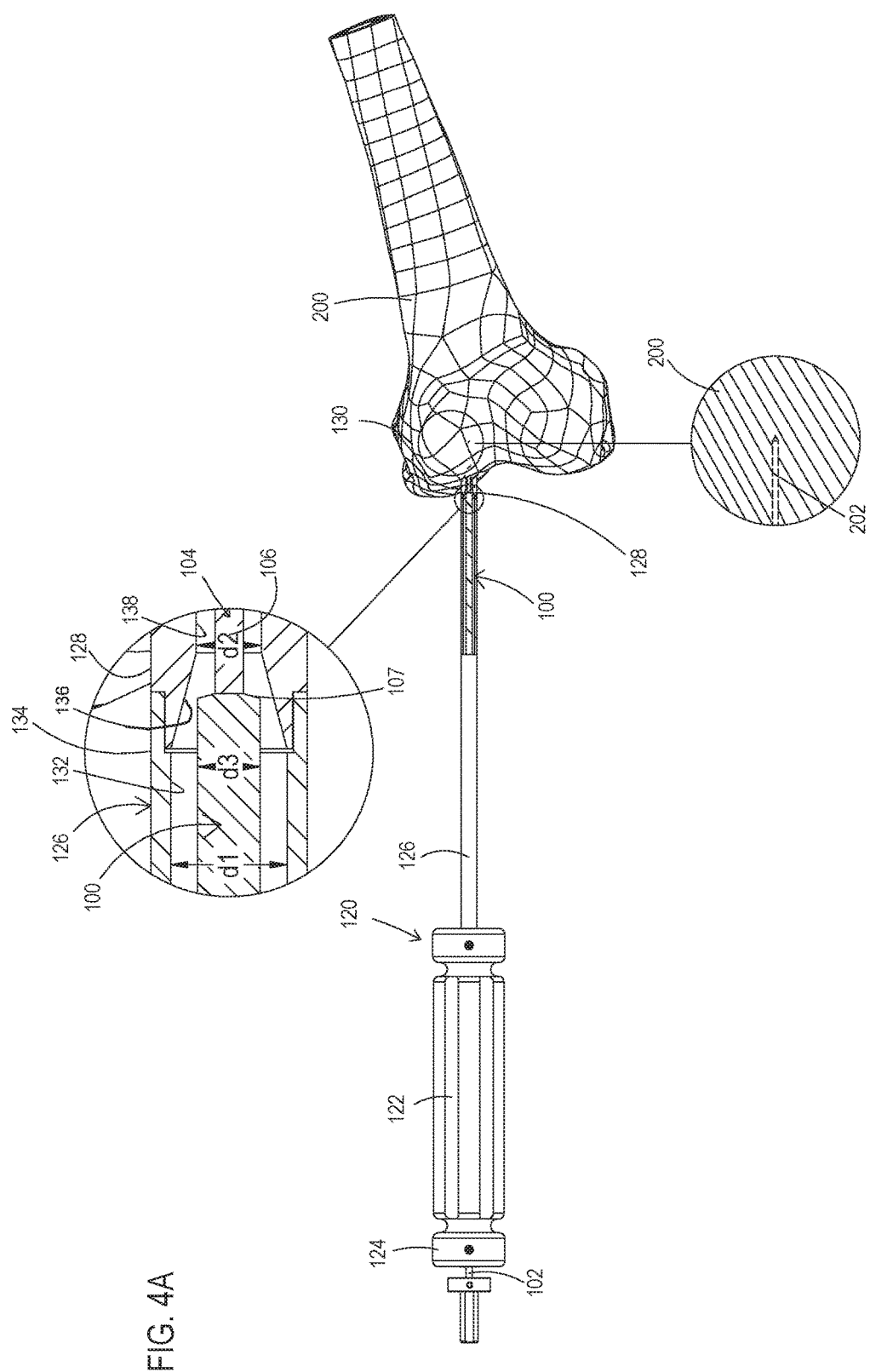
FIGS. 4A and 4B are a partial cut away side view illustration and an enlargement view and cross section view simplified illustrations of a bone material removal device of FIG. 1 inserted into a cannula, showing a first operative drilling orientation within the bone of a patient.

Reference is now made to FIG. 4A, which is a partial cut away side view illustration and an enlargement view of the bone material removal device 100 of FIG. 1 inserted into cannula 126, showing a first operative drilling orientation within bone 200 of a patient.

Cannula 126 may have a proximal cylindrical portion 134 having an inner circumference 132 including a first diameter (d1), an inwardly tapered portion 136 located adjacent to a distal end 128 of cannula 126 and a cylindrical portion 138 having an inner circumference having a second diameter (d2) and located at the distal end 128 of cannula 126. It is appreciated that the first diameter of portion 134 inner circumference 132 may be substantially greater than the second diameter (d2) of distalmost cylindrical portion 138 at distal end 128. The outer diameter (d3) of bone material removal device 100, excluding distal end 104, may be substantially equal to second diameter (d2) of the inner circumference of cylinder 138 of distal end 128 of cannula 126, so that to support primarily axial and rotational movement and minimal to no movement of device 100 in a radial direction within distal portion 128 inner circumference (d2) of cylindrical portion 138.

Reference is now made to FIGS. 4A, 4B, 5A, 5B and 5C which are cross-section view simplified illustrations of examples of operative stages of bone material removal device 100 at various points in time as it is advanced distally into the patient's bone 200. It will become apparent to persons skilled in the art that the operating stages of FIGS. 4A-5B disclosed hereinbelow demonstrate conversion of bone material removal device 100 from a bore-drilling device to an undercut producing device by conversion of axial movement of device 100 to radial translation and extension of one or more carving edges of protrusion 100 for example, by means of transition of device 100 from a resting state to a stressed state or vice versa. These steps may be commonly carried out in a continuous fashion.

As illustrated in FIG. 4A and described above, a freedom degree exists between bone material removal device 100 and cannula 126 that allows the bone material removal device 100 to be advanced distally longitudinally along longitudinal axis 105 due to the elastic characteristics of the bone material removal device 100. The freedom degree is created due to the fact that the outer diameter (d3) of the remainder of bone material removal device 100, i.e., the thickest portion of the device 3 100, except of the distal end 104 is substantially smaller than the first diameter (d1) of the proximal cylindrical portion 134 of the cannula 126.

Figure 4B:
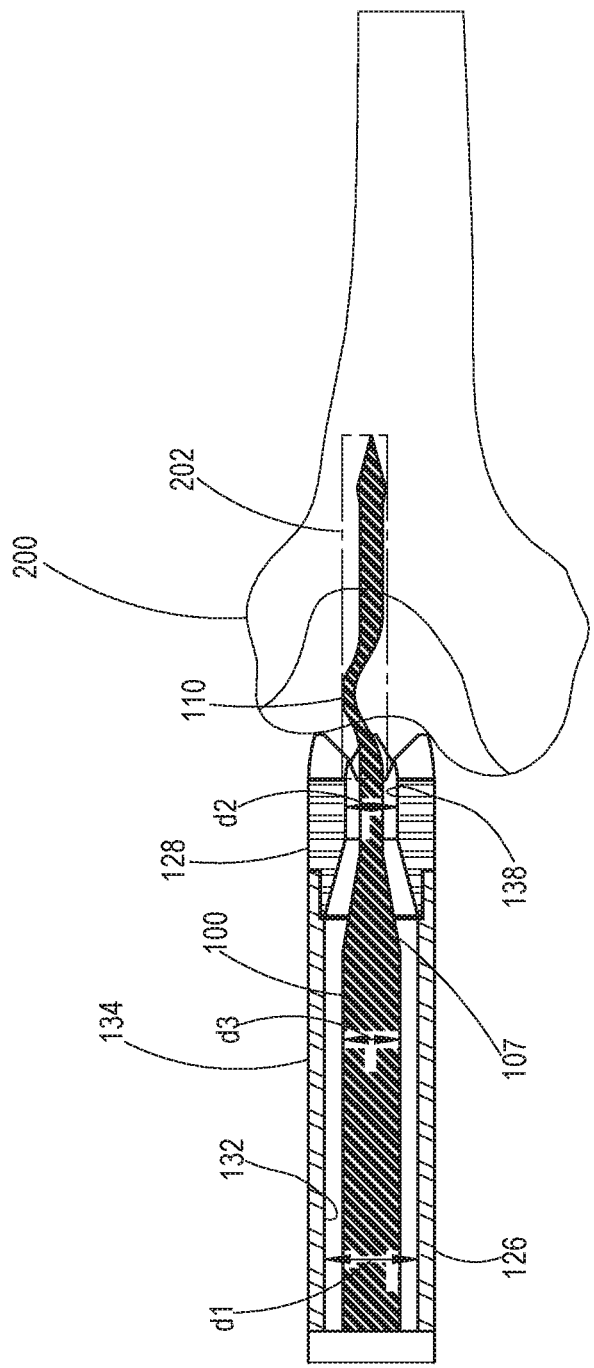

As shown in FIG. 4B, at the point in time of the stage of insertion of bone material removal device 100 depicted in FIG. 4A, device 100 may be free to move radially within cannula 126 inner circumference 132 so that a point of contact (not shown) of portion 134 inner circumference 132 with bone material removal device 100 can form a first shaft capture wherein the bone surrounding drilling tip 116 (i.e., bore 202, FIGS. 5A, 5B and 5C) may form a second shaft capture. The specific location of the first point of contact (capture) may vary throughout the drilling process. The distance between the first and second shaft captures may create a first bending moment on bone material removal device 100 that elastically deforms device 100 into a stressed state such as that depicted in FIG. 2. In this state, the elastic characteristics of device 100 bring protrusion 110 to succumb to bending forces thereupon and bend to become aligned with longitudinal axis 105 and with first cylindrical portion 106 and second cylindrical portion 108, conforming to the diameter of a bore drilled by bore drilling tip 116 thus providing for longitudinal advancement of the device 100 within the bone 200 of the patient and thus formation of a small diameter bore therewithin.

It is a particular feature of an embodiment of the present invention, in some embodiments thereof, that at this stage first cylindrical portion 106, second cylindrical portion 108 and protrusion 110 are mutually aligned along longitudinal axis 105 having a diameter equal or less than the radius of a bore drilled by bore drilling tip 116 during the operative orientation shown in FIGS. 4A and 4B, while distally facing shoulder 107 does not yet engage the distalmost cylindrical portion 138 of the cannula 126.

It is seen in FIGS. 4A and 4B that distal advancement of the bone material removal device 100 results in a straight longitudinal bore 202 in the patient's bone 200.

The longitudinal bore 202 that is formed in this operative orientation optionally has a diameter in the range of 2 mm-4 mm, alternatively and optionally in the range of 1.5 mm-3 mm and alternatively and optionally in the range of 1 mm-2 mm, corresponding to the outer diameter of first cylindrical portion 106 and second cylindrical portion 108.

Figure 5A:
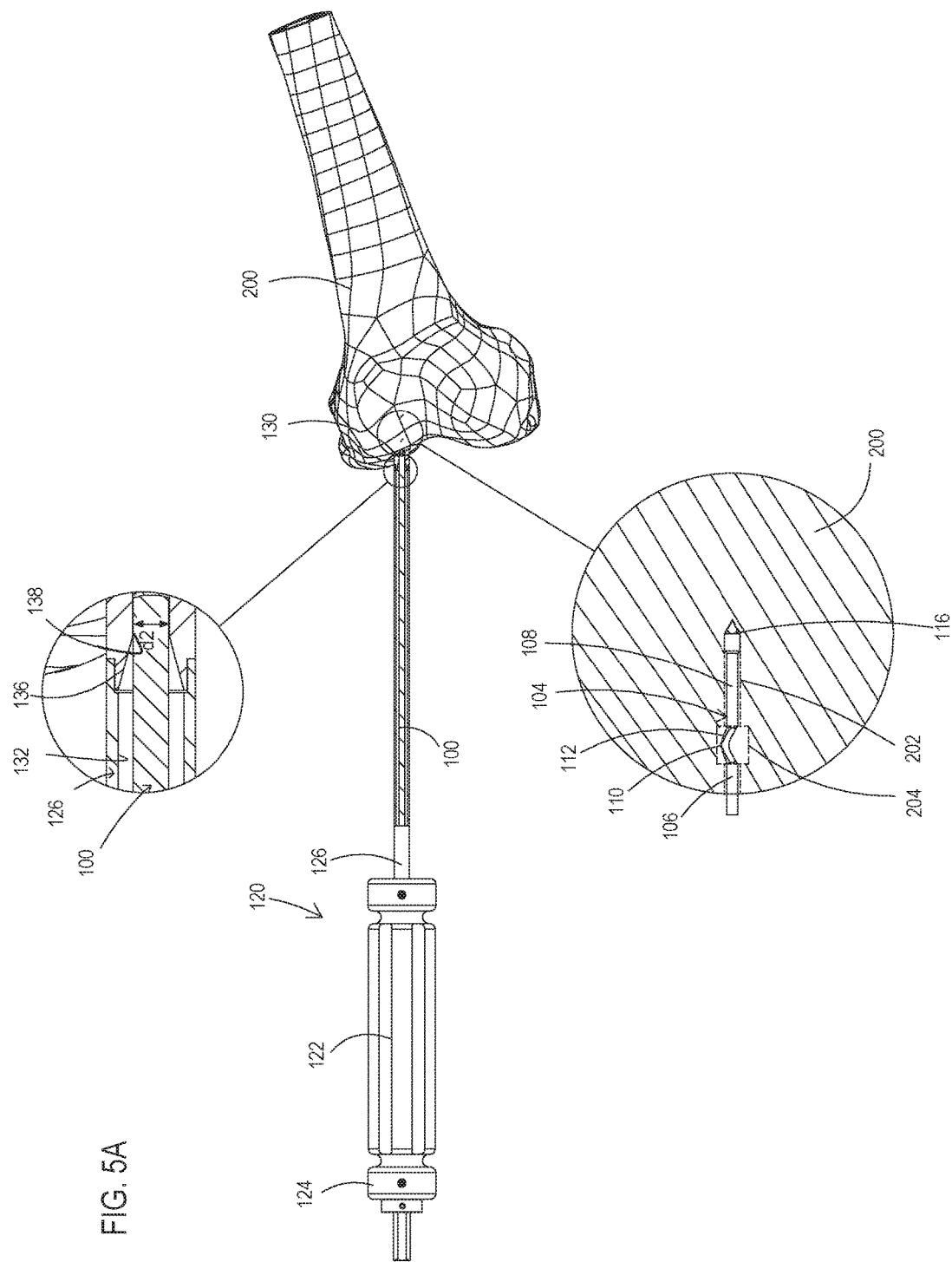
FIGS. 5A, 5B and 5C are a partial cut away side view illustration and an enlargement view and cross section view simplified illustrations of a bone material removal device of FIG. 1 inserted into a cannula, showing a second operative drilling orientation within the bone of a patient.
Figure 5B:
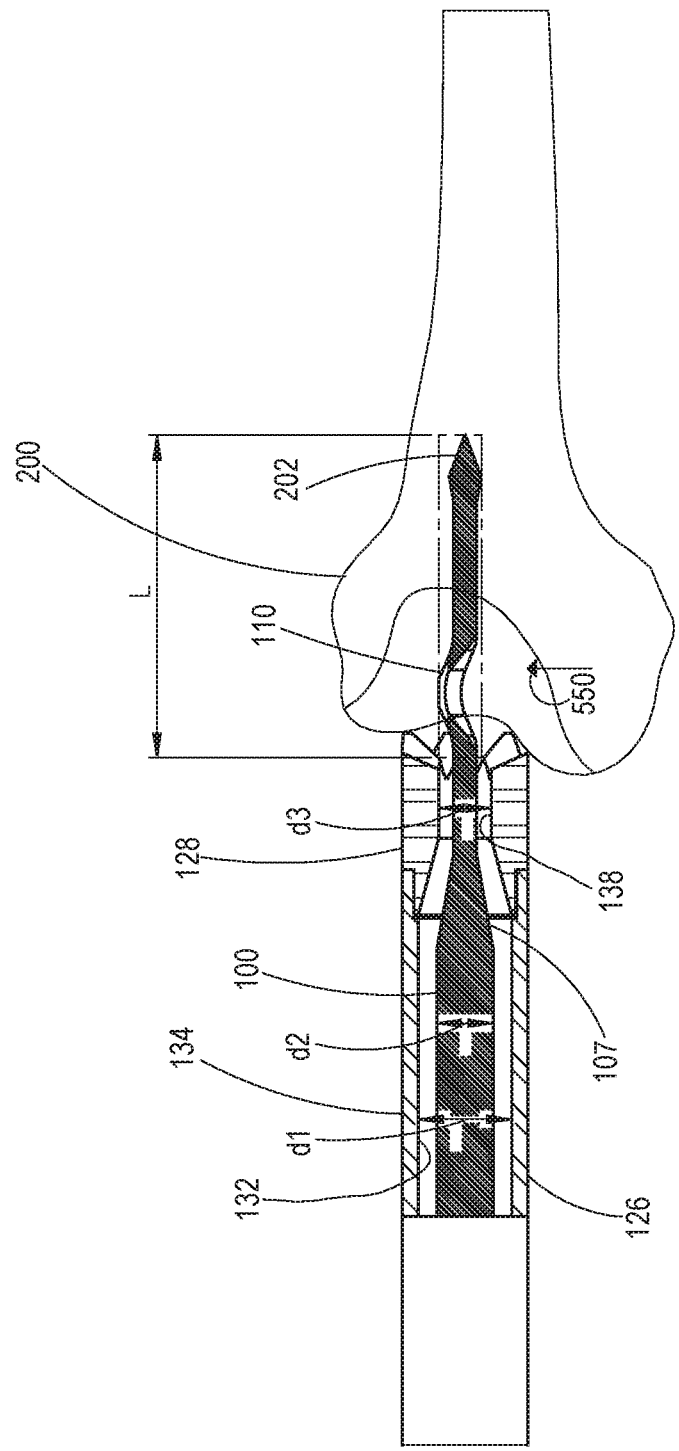
Figure 5C:
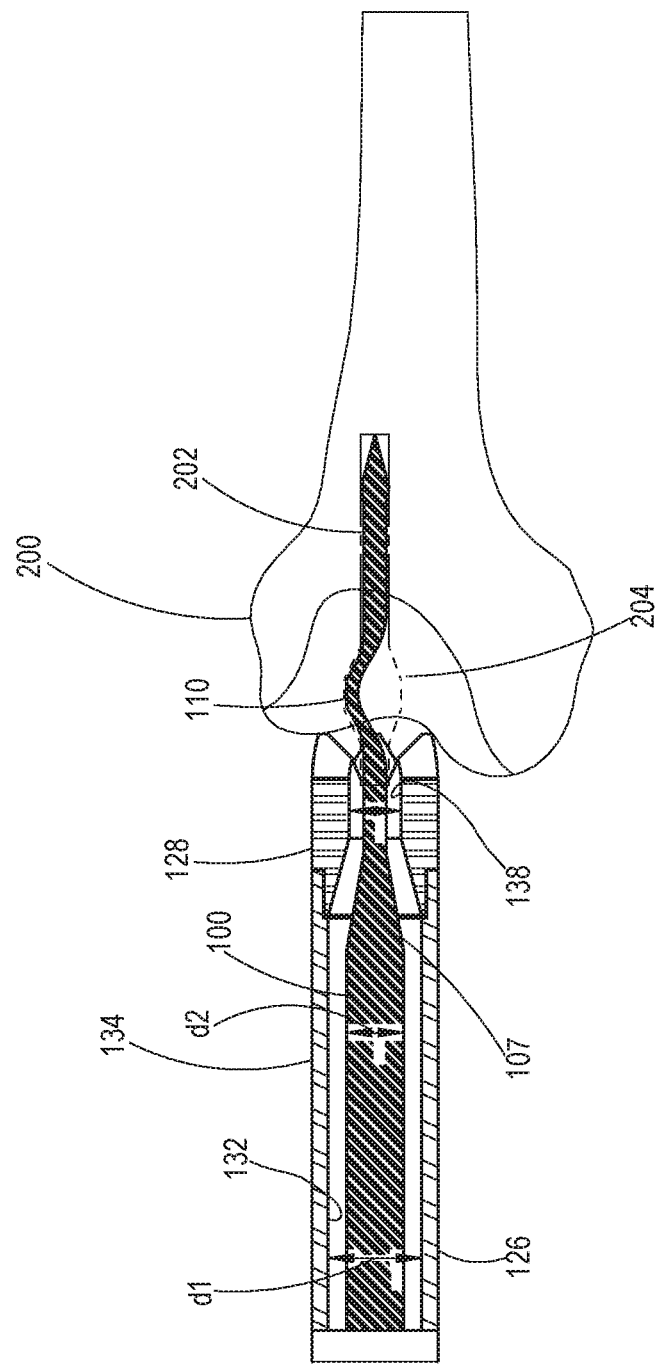

Reference is now made to FIGS. 5A, 5B and 5C, which are partial cut away side view illustration and an enlargement view and cross-section view simplified illustrations of the embodiment of bone material removal device 100 of FIG. 1 inserted into cannula 126, showing a second operative drilling orientation within the bone 200 of a patient.

It is seen in FIG. 5A that the bone material removal device 100 is advanced further distally into the patient's bone 200. Further distal advancement of the bone material removal device 100 can be in the range of approximately 1 mm-8 mm, alternatively and optionally 1.5 mm-7 mm and alternatively and optionally from 2 mm-6 mm.

It is a particular feature of an embodiment of the present invention that at this stage, as shown in FIG. 5A and in greater detail in FIG. 5B, shoulder 107 and a portion of device 100 proximal thereto has been further moved axially and entered distalmost cylindrical portion 138 of the cannula 126 in which no radial freedom degree exists anymore between the bone material removal device 100 and cannula 126.

The freedom degree is lost due to the fact that the outer diameter of the remainder of a bone material removal device 100 except of the distal end 104 engages the substantially equal diameter of the distalmost cylindrical portion 138 of the cannula 126.

At this point in time, the bone surrounding drilling tip 116 (i.e., bore 202) may remain a second shaft capture but distalmost cylindrical portion 138 becomes a third shaft capture replacing the second shaft capture located at a contact point along portion 134 inner circumference 132. The distance between the first and third shaft captures, being shorter than the distance between the second and first shaft captures, may create a second smaller bending moment on bone material removal device 100 down to a threshold length designated in FIG. 5B with the letter (L) (e.g., the tip of the cannula) at and below which distal end 104 becomes fully rigid.

The increase in rigidity (decrease in bending moment) and the shape memory characteristics of the material of which bone material removal device 100 is made, tend to return device 100 to its original resting state such as that shown in FIG. 1, thus placing radially directed force on protrusion 110 indicated in FIG. 5B by an arrow designated reference numeral 550 and urging protrusion 110 to extend radially. It is therefore a particular feature of an embodiment of the present invention that axial movement of the bore widening element in the form of protrusion 110 relative to cannula 126 increases the rigidity of distal end 104 and radially extends the carving portion of protrusion 110 to a radially extended position.

As illustrated in FIG. 5C the increased rigidity of distal end 104 brings protrusion 110 to extend radially and to perform an undercut within the bone 200 of a patient by means of rotation about longitudinal axis 105, increasing in diameter and creating a bore (undercut) 204 having a diameter, which is substantially larger than the diameter of bore 202. Due to the rigid characteristics of the bone material removal device 100 at this stage, protrusion 110 protrudes radially externally to longitudinal axis 105, thus providing for longitudinal advancement of the bone material removal device 100 within bone 200 of the patient and thus formation of a large diameter bore therewithin, corresponding to the outer diameter formed by protrusion 110.

It is a particular feature of an embodiment of the present invention that at this point in time, first cylindrical portion 106 and second cylindrical portion 108 are mutually aligned along longitudinal axis 105 during the operative orientation shown in FIGS. 5A-5C and that protrusion 110 extends radially outwardly with respect to longitudinal axis 105 since the distally facing shoulder 107 engages the distalmost cylindrical portion 138 of the cannula 126 and prevents from the protrusion 110 to lose rigidity.

Undercut 204 that is formed in the operative orientation shown in FIGS. 5A-5C optionally has a diameter in the range of 0.6 mm-3.2 mm, alternatively and optionally 1 mm-2.8 mm and alternatively and optionally 1.2 mm-2.4 mm, corresponding to the outer diameter of the protrusion 110 in its most radially extended configuration.

It is seen in FIGS. 5A-5C that further distal advancement of the bone material removal device 100 results in formation of an undercut 204 generally in the middle of the straight longitudinal bore 202 formed in the patient's bone 200.

Figure 6:
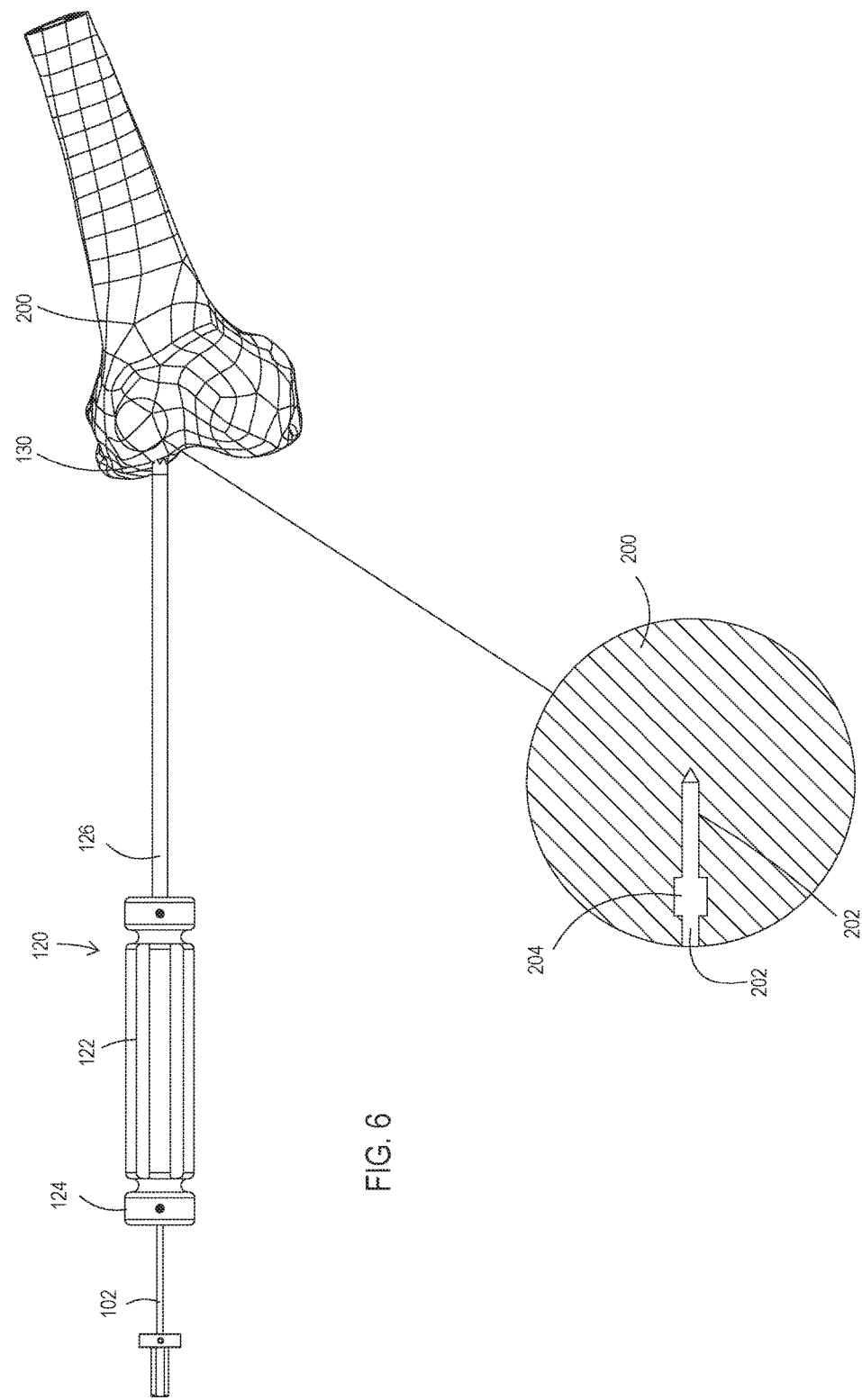
FIG. 6 is a partial cut away side view illustration and an enlargement view of a bone material removal device of FIG. 1 inserted into a cannula, showing removal of the bone material removal device from the bone of a patient.

Reference is now made to FIG. 6, which is a partial cut away side view illustration and an enlargement view of the embodiment of the bone material removal device of FIG. 1 inserted into the cannula 126, showing removal of the bone material removal device 100 from the bone 200 of a patient.

It is seen in FIG. 6 that the bone material removal device 100 has been withdrawn from the patient's bone 200, leaving the bone with formed bore having varying diameters, longitudinal bore 202 of a smaller diameter and undercut 204 of a larger diameter.

Figure 7:
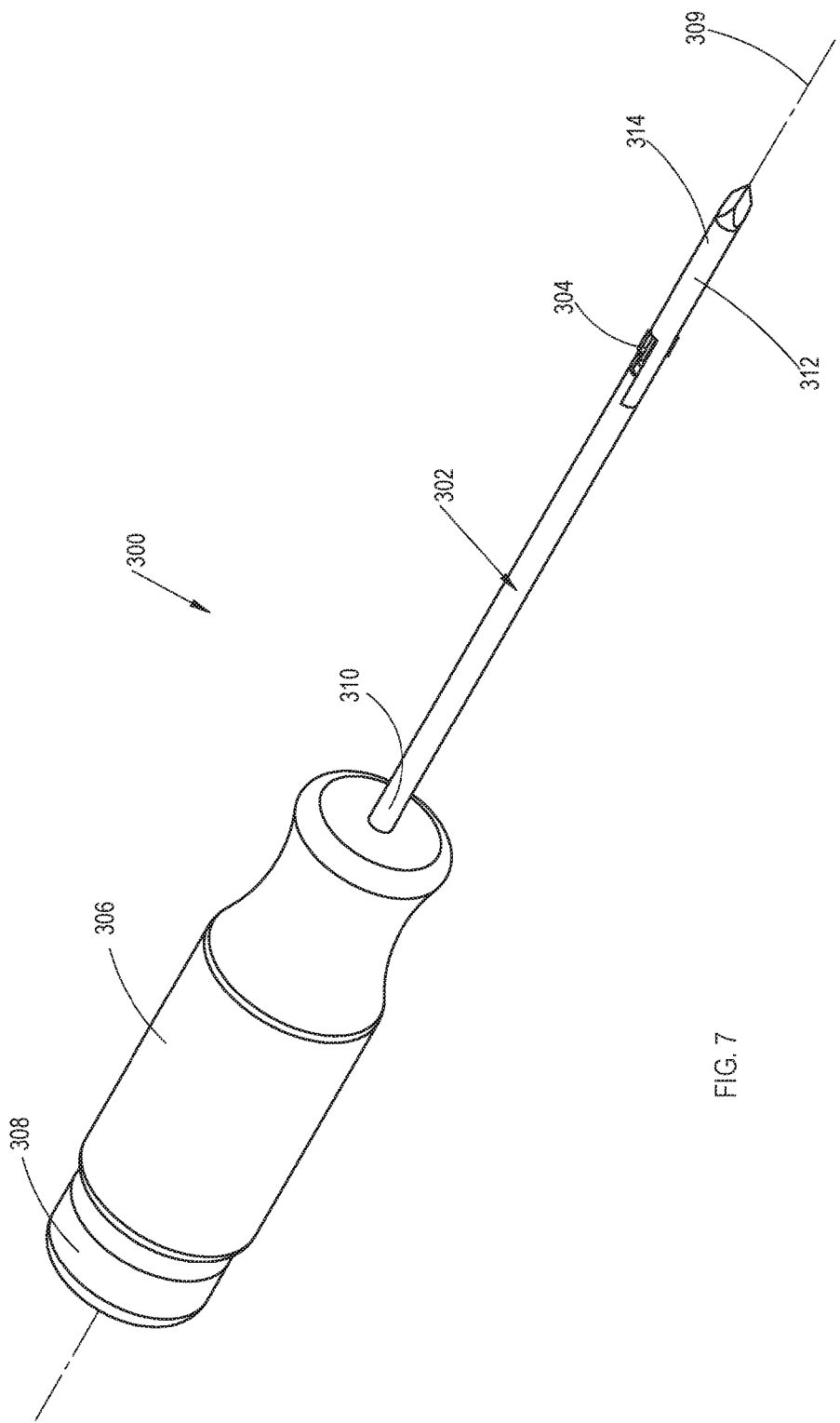
FIG. 7 is a simplified pictorial illustration of a bone material removal device constructed and operative in accordance with an embodiment of the present invention.

Reference is now made to FIG. 7, which is a simplified pictorial illustration of a bone material removal device 300 constructed and operative in accordance with an additional embodiment of the present invention.

It is seen in FIG. 7 that bone material removal device 300 optionally includes a drilling element 302 optionally having a form of a cannula and having a proximal end 310 and a distal end 312 and formed of a biocompatible metal. Distal end 312 may be sealed by a tapered drilling tip 314. Drilling element 302 may optionally have a diameter in the range 2 mm-4 mm, alternatively and optionally in the range of 1.5 mm-3 mm and alternatively and optionally in the range of 1 mm-2 mm. Device 300 may also include a bore widening element 304 disposed between distal end 312 and proximal end 310 of drilling element 302 and be at least partially inserted therein.

Drilling element 302 connects at proximal end 310 to a handle 306 having a pushing element 308 inserted therein in contact with bore widening element 304. Alternatively and optionally, drilling element 302 and bore widening element 304 can be connected to a power tool, e.g., a power drill. Drilling element 302 and the bore widening element 304 are arranged along a mutual longitudinal axis 309.

It is a particular feature of an embodiment of the present invention that the bore widening element 304 may be at least partially inserted into the drilling element 302 and be selectively positioned in a closed position enabling drilling a bore of a first diameter within the bone of a patient and in an open, radially extended position enabling drilling a bore of a second diameter within the bone of a patient, wherein the first diameter may optionally be equal to the outer diameter of the tubular or cannula portion of the drilling element 302 and the second diameter may be greater than the first diameter, thus forming an undercut within the bone of a patient.

Figure 8A:
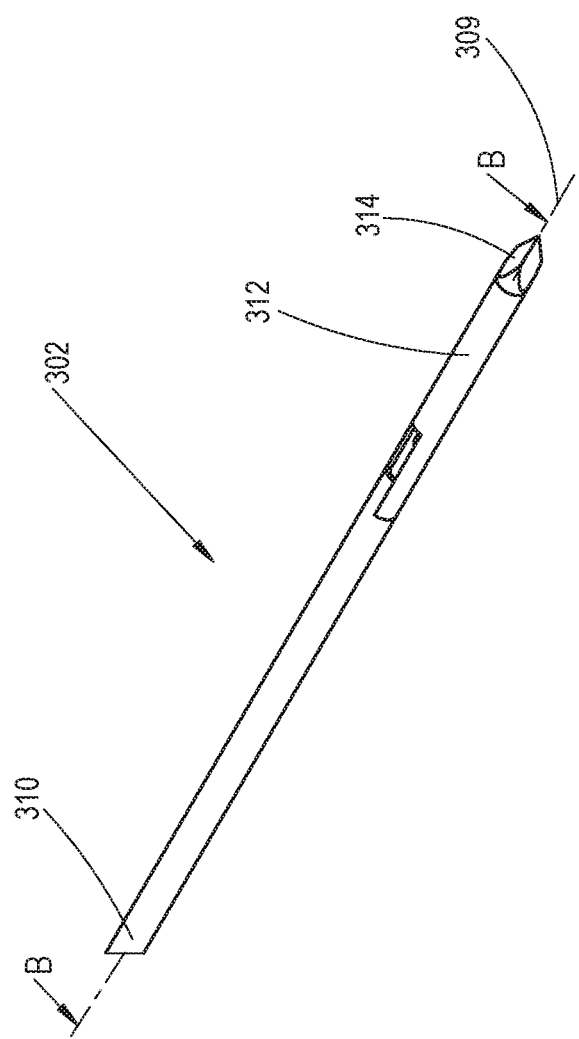
FIG. 8A is a simplified pictorial illustration of a drill element of the bone material removal device of FIG. 7.
Figure 8B:
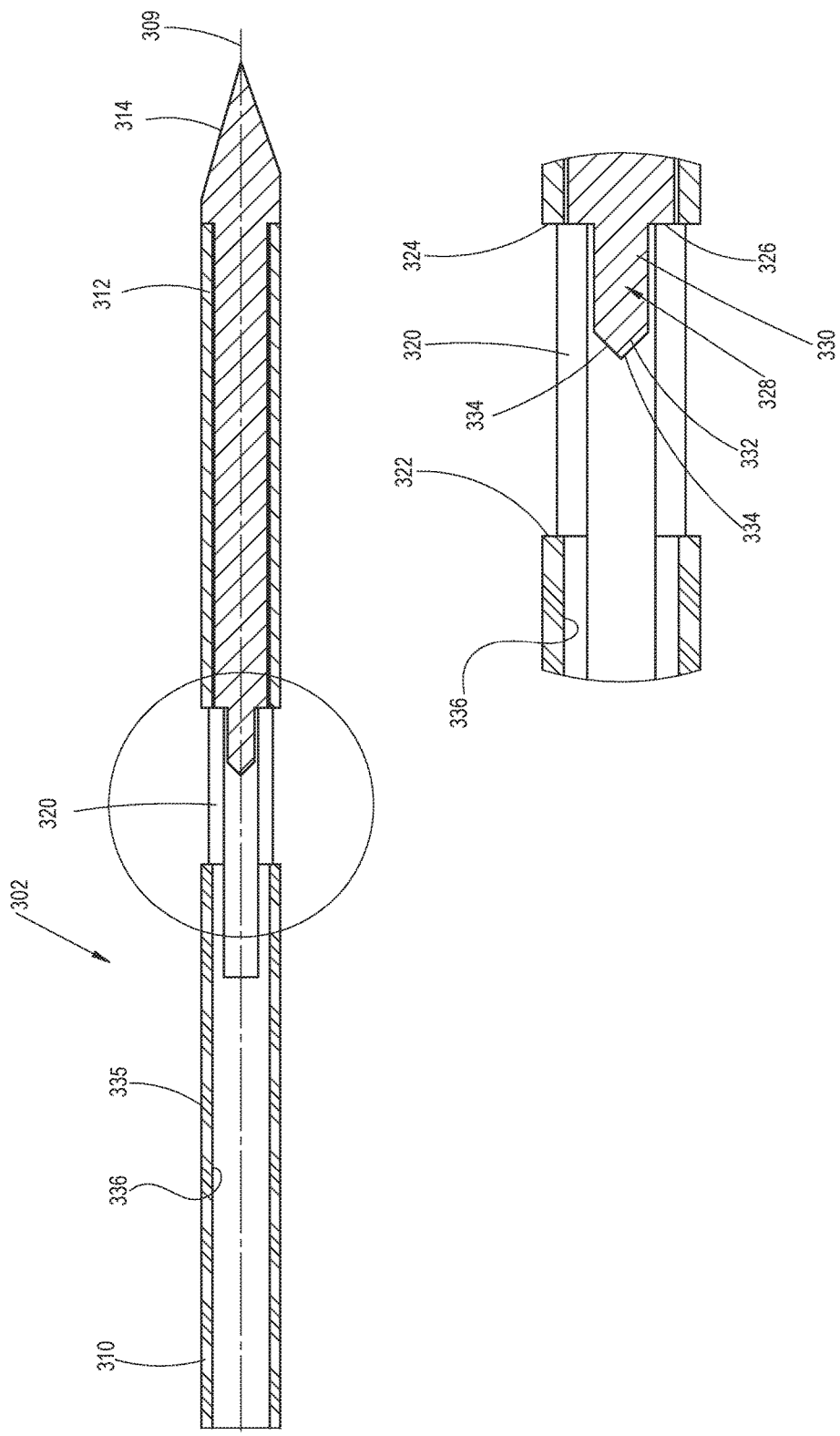
FIG. 8B is a simplified cross sectional view illustration and an enlargement thereof of the drill element of FIG. 8A, section being taken along lines B-B in FIG. 8A.

Reference is now made to FIG. 8A, which is a simplified pictorial illustration of the drill element 302 of the bone material removal device 300 of FIG. 7, and to FIG. 8B, which is a simplified cross sectional view illustration and an enlargement thereof of the drilling element 302 of FIG. 8A, section being taken along lines B-B in FIG. 8A.

Drilling element 302 may optionally be integrally made of a biocompatible material (e.g., metal) and arranged along longitudinal axis 309.

It is seen in FIGS. 8A & 8B that one or more through openings 320 in a wall 335 of drilling element 302 radially extend through drilling element 302 transversely to longitudinal axis 309. An inner surface 336 of drilling element 302 wall 335 defines a hollow portion of drilling element 302 proximally to opening 320 and optionally solid distally to opening 320.

Each of the openings 320 longitudinally extends from a distally facing shoulder 322 to a proximally facing shoulder 324.

It is appreciated that the drilling tip 314 can be fixedly coupled to the drilling element 302 or alternatively integrally made therewith.

In the example seen in FIG. 8B the solid part of the drilling element 302 extends proximally from the drilling tip 314 to approximately adjacent the proximally facing shoulder 324 and defines a proximally facing surface 326 at this location. A protrusion 328 optionally extends proximally from surface 326. The protrusion 328 shown in FIG. 8B optionally has a cylindrical portion 330 and a proximal portion 332 having one or more inclined surfaces (e.g., conical or tapered) proximally extending therefrom. It is appreciated that protrusion 328 can alternatively be formed as a cone along its entire longitudinal extent or any other widening geometry, for example pyramidal or any other suitable shape. In accordance with the exemplary embodiment of the present invention shown in FIG. 8A, the conical portion 332 defines one or more distally extending tapered or inclined surfaces 334 extending in one or more radial directions. For example, conical portion 332 may define two distally extending tapered or inclined surfaces 334 extending in mutually opposite radial directions.

The hollow part of the drilling element 302 defines an outer surface 335 and an inner surface 336.

Figure 9A:
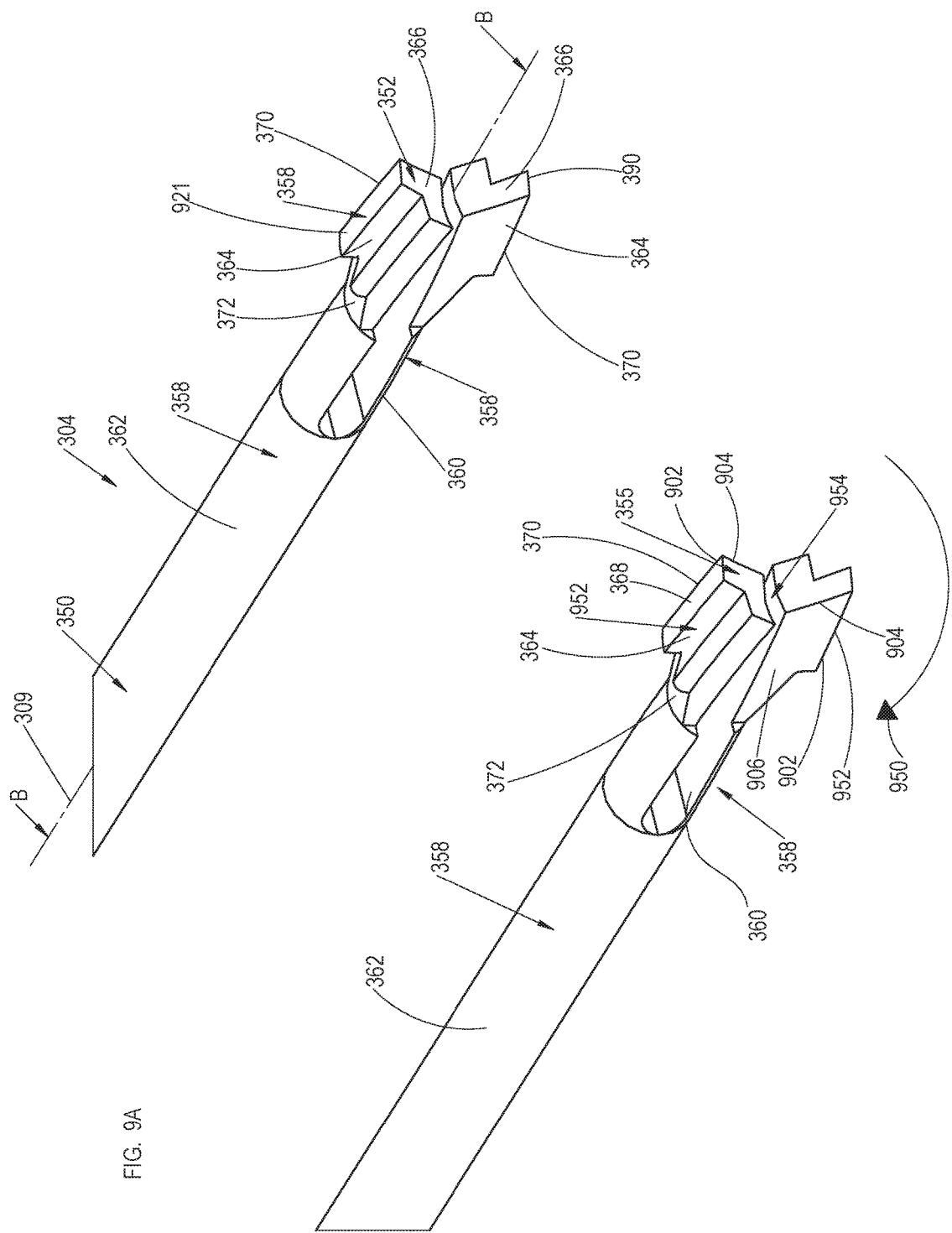
FIG. 9A is a simplified pictorial and cross section view illustration of a bore widening element of the bone material removal device of FIG. 7.
Figure 9B:
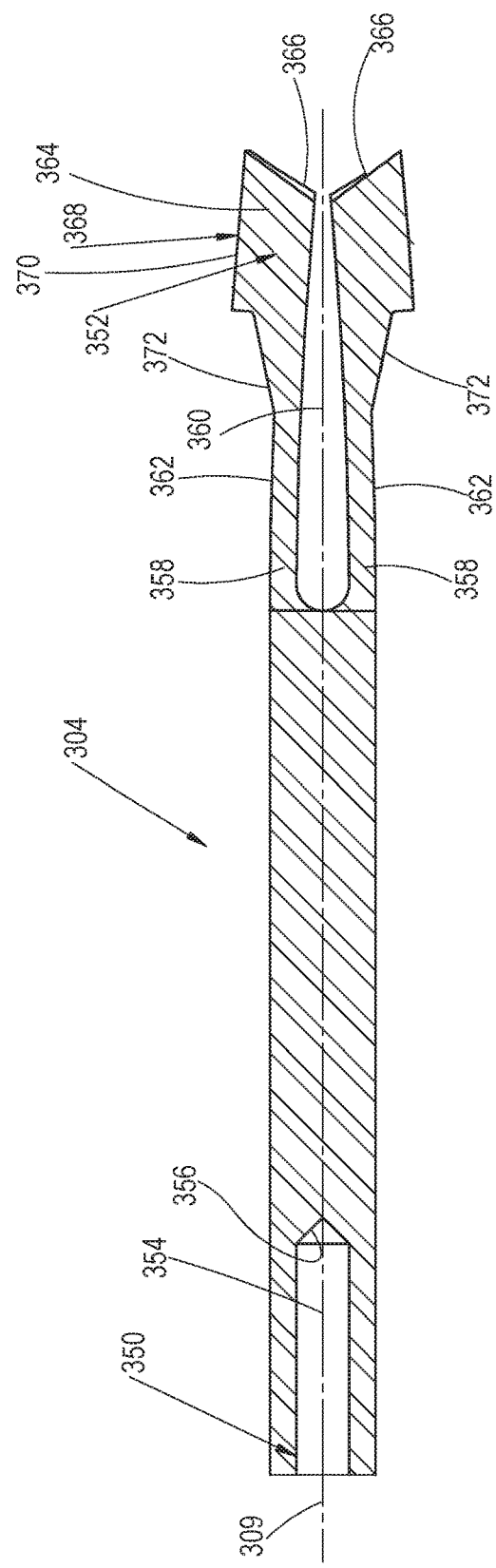
FIG. 9B is a simplified cross sectional view illustration of the bore widening element of FIG. 9A, section being taken along lines B-B in FIG. 9A.

Reference is now made to FIG. 9A, which is a simplified pictorial and cross section view illustration of an example of bore widening element 304 of the bone material removal device 300 of FIG. 7 and to FIG. 9B, which is a simplified cross sectional view illustration of bore widening element 304 of FIG. 9A, section being taken along lines B-B in FIG. 9A.

Bore widening element 304 optionally has a proximal end 350 and a distal end 352 and can be integrally made of an elastic biocompatible material having shape memory qualities material (e.g., metal) and be arranged along longitudinal axis 309.

It is particularly seen in FIG. 9B that a generally cylindrical recess 354 is formed at the proximal end 350 to be engaged by pushing element 308 (FIG. 7), distally extends therefrom and terminates at a proximally facing surface 356.

Optionally, one or more distally extending arms 358 may extend from approximately the middle of the longitudinal extent of bore widening element 304 to the distal end 352, centrally facing surfaces thereof bordering and separated by a longitudinal recess 360 having a proximal closed end and a distal open end. Each of the arms 358 defines an outer surface 362.

As shown in FIGS. 9A and 9B, bore widening element 304 arms 358 do not parallel each other and may gradually approach and in some examples contact each other distally from the proximal closed end of longitudinal recess 360. As will be described in greater detail below, in one embodiment, bore widening element 304 depicted in FIGS. 9A and 9B may be in a resting, unstressed state so that arms 358 can be deflected inwardly one towards the other when force is exerted on outer surface 362 in a radially inward direction. Arms 358 can be deflected outwardly to be further separated one from each other when force is exerted on the inner surface of the arms 358 in a radially outward direction. In an additional embodiment, bore widening element 304 depicted in FIGS. 9A and 9B may be in a stressed or loaded state.

Each of the arms 358 defines a widened portion 364 at the distal end 352 of the widening element 304. Each of the widened portions 364 preferably defines a distally facing preferably inwardly proximally tapered or inclined surface 366. Inwardly proximally tapered or inclined surface 366 define a distal aspect of carving portions 368 proximally extending from surfaces 366. Carving portions 368 are generally longitudinal widened defining an outer carving edge 370 or several carving edges 370 as will be explained in greater detail below and a radially positioned curved surface 921 bordered at one side thereof by carving edge 370 and forming an end relief or clearance curve that prevents the rubbing of carving portions 368 against the bone, reducing the amount of force (e.g., torque) required for operation of device 300. Longitudinal carving portions 368 are joined with outer surfaces 362 of arms 358 by a generally proximally inwardly tapered or inclined surface 372. It is appreciated that the longitudinal carving portions 368 can be cylindrical or alternatively can be conical or have any other suitable shape.

It is appreciated that widened portions 364 may be generally positioned at an angle with respect to each other.

In some embodiments, bore widening element 304 may have a single arm 358 carrying one or more carving portions 368. In other embodiments, bore widening element 304 may have more than one arm only one of which carrying one or more carving portions 368.

Reference is now made to FIGS. 10A-10D, collectively referred to as FIG. 10, FIG. 11 and FIGS. 12A-12D, collectively referred to as FIG. 12, which are simplified illustrations of examples of operative stages of bone material removal device 300 at various points in time as it is advanced distally into the patient's bone 200. It will become apparent to persons skilled in the art that the operating stages disclosed hereinbelow demonstrate conversion of bone material removal device 300 from a bore-drilling device to an undercut producing device by conversion of axial movement of device 300 to radial translation and extension of one or more carving portions of bore widening element 304 arm 358 through one or more openings 320, for example, by means of transition of device 300 from a resting state to a stressed state or vice versa. These steps may be commonly carried out in a continuous fashion.

Figure 10A:
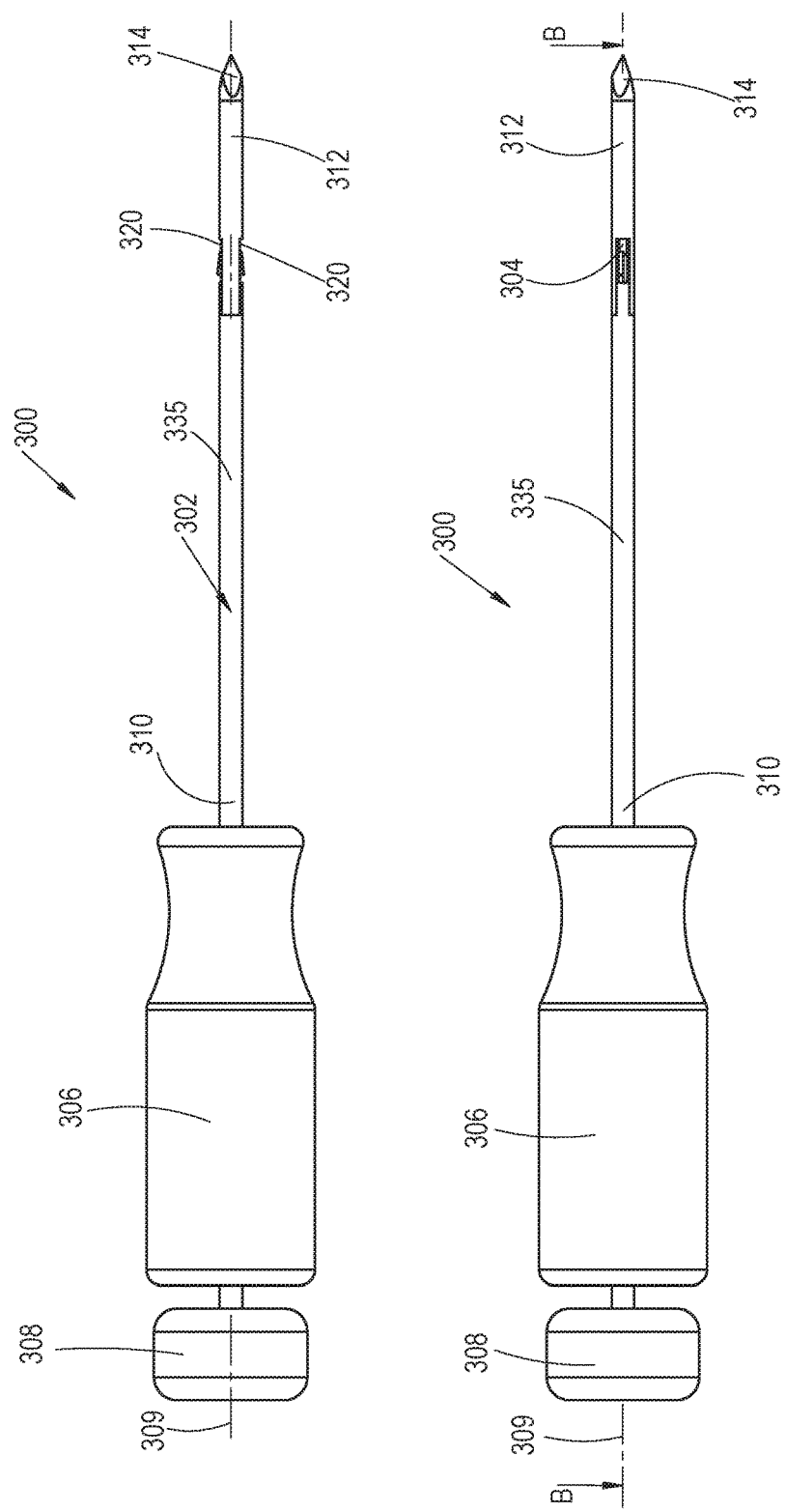
FIG. 10A illustrates two different simplified planar views, front and side views respectively, of the assembled bone material removal device of FIG. 7 in a closed operative orientation.
Figure 10B:
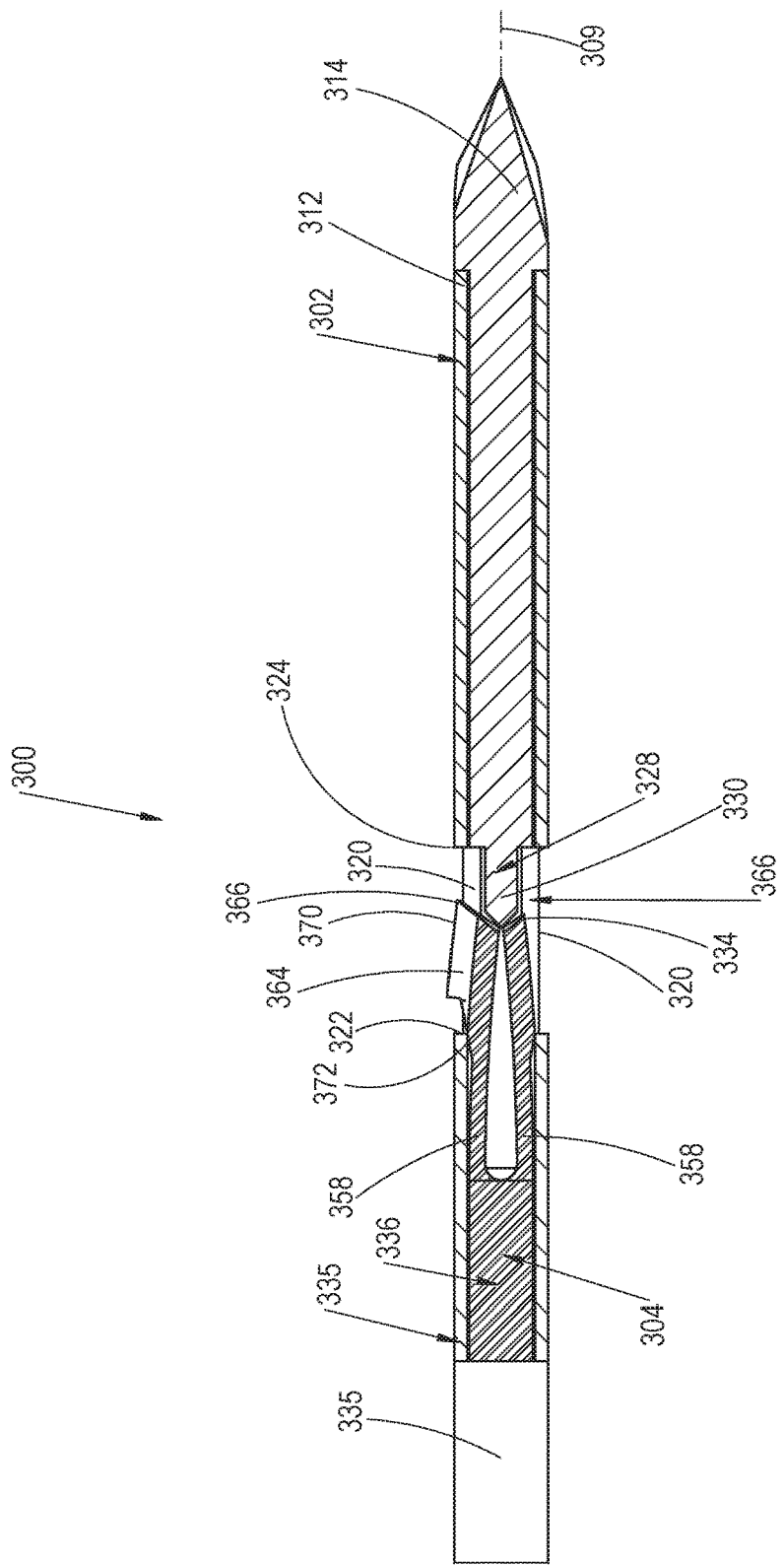
FIG. 10B is a simplified partial cross sectional view illustration of the assembled bone material removal device of FIG. 7 in the closed operative orientation, section being taken along lines B-B in FIG. 10A.
Figure 10C:
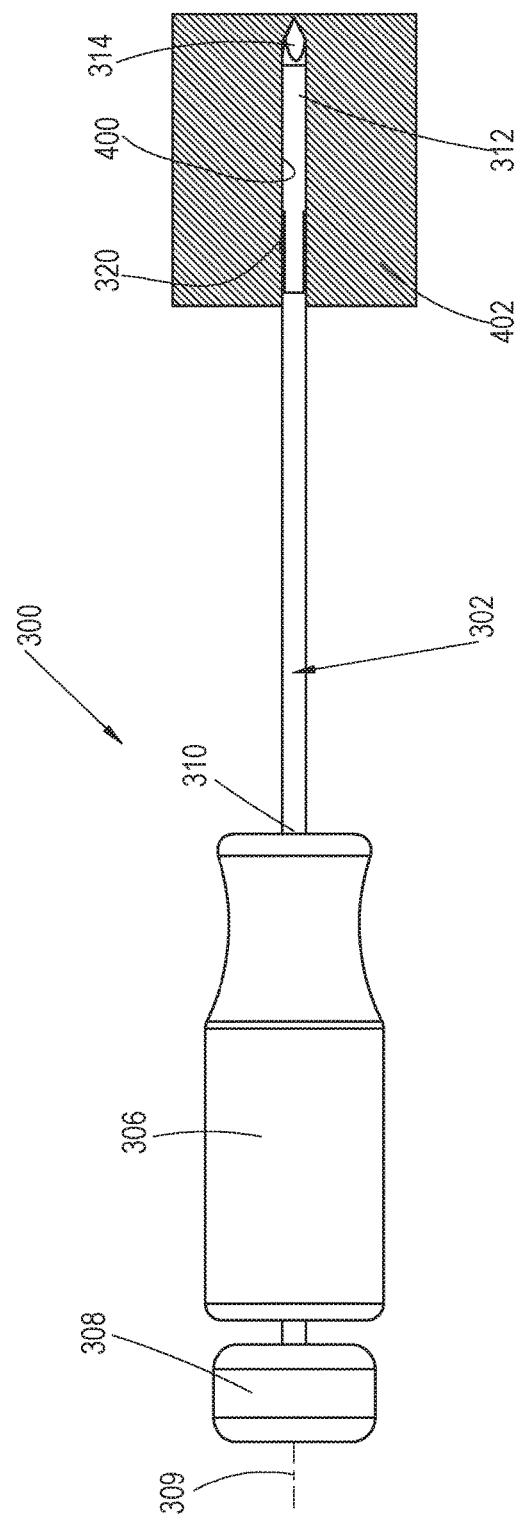
FIG. 10C is a simplified side view of the assembled bone material removal device in a closed operative orientation shown within the bone of a patient.

Reference is now made to FIG. 10A, which illustrates two different simplified planar views, front and side views respectively, of an example of the assembled bone material removal device 300 of FIG. 7 in a closed operative orientation and to FIG. 10B, which is a simplified partial cross sectional view illustration of the assembled bone material removal device 300 of FIG. 7 in the closed operative orientation, section being taken along lines B-B in FIG. 10A. Reference is additionally made to FIG. 10C, which is a simplified side view of the assembled bone material removal device 300 in a closed operative orientation shown within the bone of a patient and to FIG. 10D, which is an enlargement of FIG. 10C, illustrating the assembled bone material removal device 300 in a closed operative orientation shown within the bone of a patient.

In the example of FIGS. 10A-10D bore widening element 304 is inserted into the drilling element 302, such that they are mutually arranged along longitudinal axis 309.

It is also seen that pushing element 308 is not yet fully inserted into the handle 306, thus bore widening element 304 is positioned at rest (FIG. 10B) in a proximal location, thus providing for closed operative orientation of the bone material removal device 300. In this proximal location, pushing element 308 does not engage the proximally facing surface 356 of recess 354 of bore widening element 304.

The widened portions 364 of arms 358 of the widening element 304 are each located within the respective opening 320 of the drilling element 302, such that proximally inwardly tapered or inclined surfaces 372 are located adjacent the distally facing shoulders 322 defined by openings 320 of the drilling element 302.

The distally facing preferably inwardly proximally tapered or inclined surface surfaces 366 of the widening element 304 do not engage distally extending tapered or inclined surfaces 334 of protrusion 328 of the drilling element 302, thus the arms 358 of the widening element 304 are positioned in a closed resting state operative orientation. At this point in time, arms 358 may optionally be generally slightly radially inwardly deflected toward each other by means of inward radial force exerted by the inner surface 336 of the drilling element 302 on the proximally inwardly tapered or inclined surfaces 372 of widened portions 364 of the arms 358 of widening element 304.

It is a particular feature of an embodiment of the present invention that in the closed operative orientation of the bone material removal device 300, carving edges 370 of widening element 304 may slightly extend radially so that only to be aligned with the outer surface 337 of the drilling element 302. Thus, the drilling radius of the outer surface of the drilling element 302 is substantially equal to the drilling radius formed by the carving edges 370 of the widening element 304 thus forming an initial bore 400 of a first diameter is formed within the bone 402 of a patient particularly seen in FIGS. 10C and 10D.

The radius of the initially drilled bore can be for example in the range of 0.2 mm-1.4 mm, alternatively and optionally 0.4 mm-1.2 mm and alternatively and optionally 0.5 mm-1 mm or any other radius, preferably equal to the outer diameter of drilling element 302.

Figure 10D:
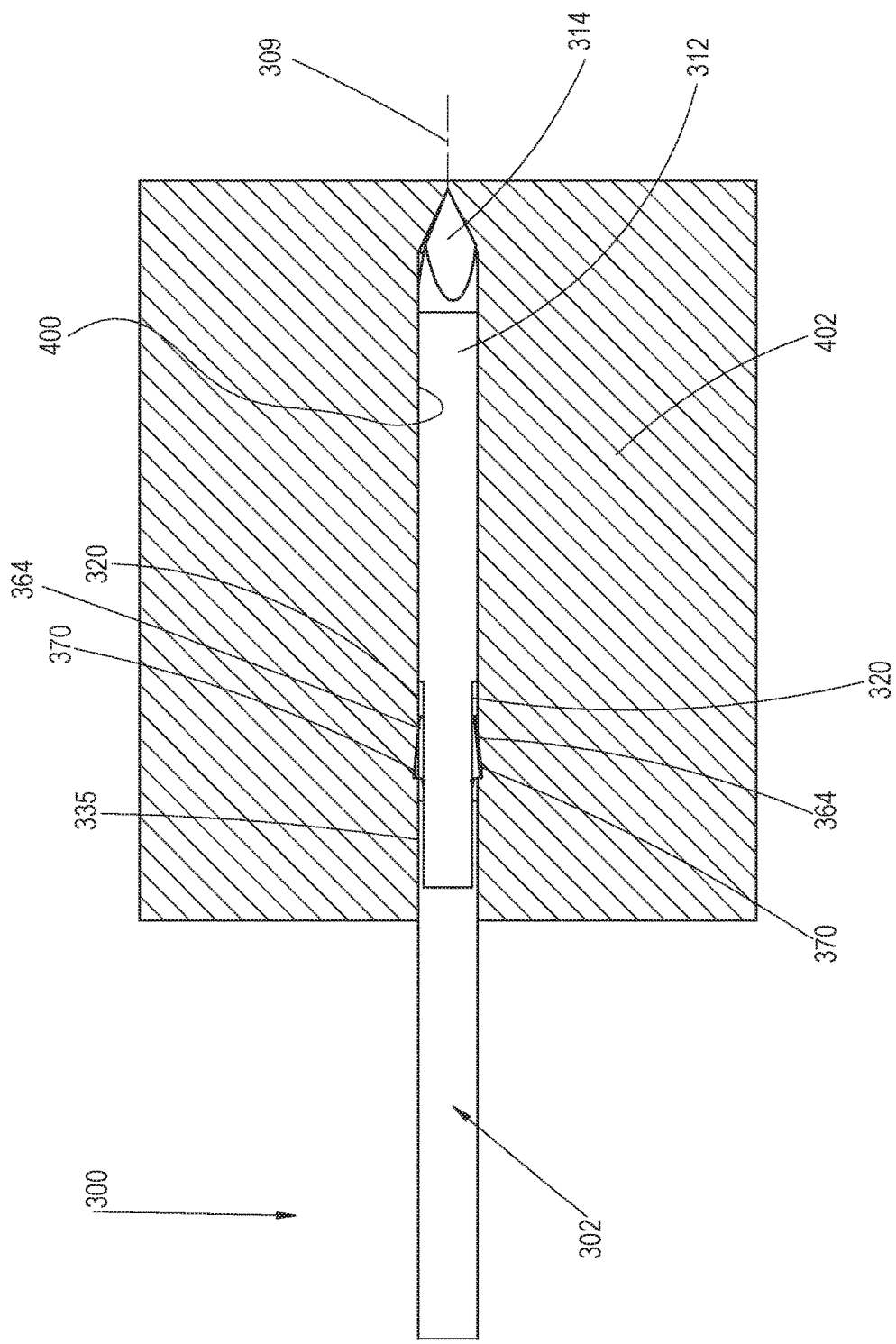
FIG. 10D is an enlargement of FIG. 10C, illustrating the assembled bone material removal device in a closed operative orientation shown within the bone of a patient.
Figure 11:
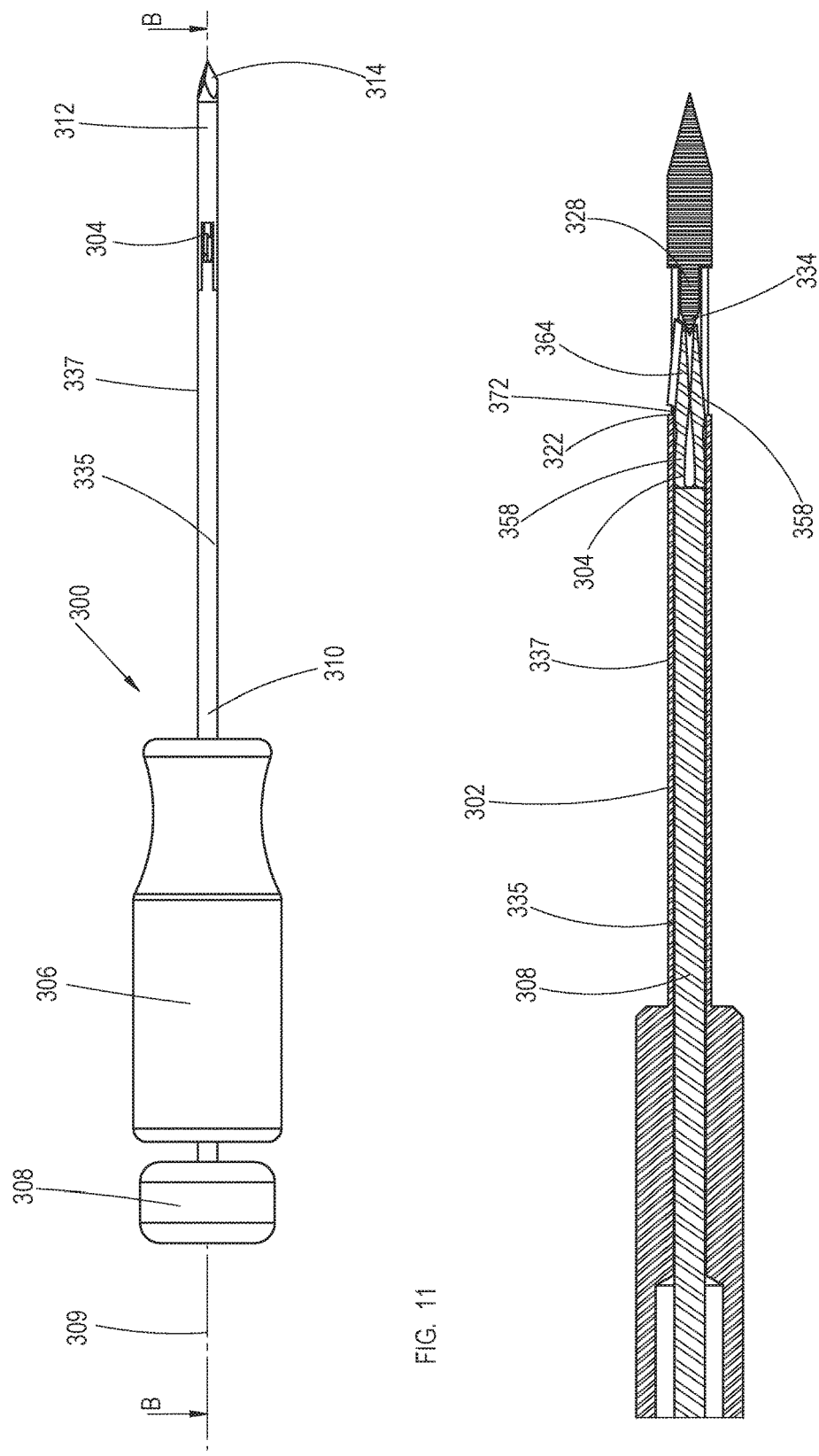
FIG. 11 is a simplified planar front and a partial cross sectional view of an example of the assembled bone material removal device of FIG. 7 in a transitional operative orientation between the closed orientation position of FIGS. 10A-D and open orientation of FIGS. 12A-D.

FIG. 11, which is a simplified planar front and a partial cross sectional view of an example of the embodiment of assembled bone material removal device 300 of FIG. 7 in a transitional operative orientation between the closed orientation position of FIG. 10A-10D and open orientation of FIGS. 12A-12D.

At the point in time shown in FIG. 11, pushing element 308 has been partially advanced axially distally and is partially inserted into handle 306, such that its distal end engages bore widening element 304, axially displacing bore widening element 304 distally to be partially engaged by protrusion 328 tapered or inclined surfaces 334.

Pushing element 308 may attach and lock into recess 354 by quick release coupling system or alternatively and optionally by a threaded mechanism allowing to axially gradually move widening element 304 as desired by turning pushing element 308.

Axially distally displaced bore widening element 304 may move axially and engage distally extending tapered or inclined surfaces 334 of protrusion 328, which geometrically interfere with the axial movement of bore widening element 304 and may exert radially directed bending force on arms 358 of bore widening element 304 bringing the carving portions to travel and extend radially and outwardly through one or more openings 320.

Figure 12A:
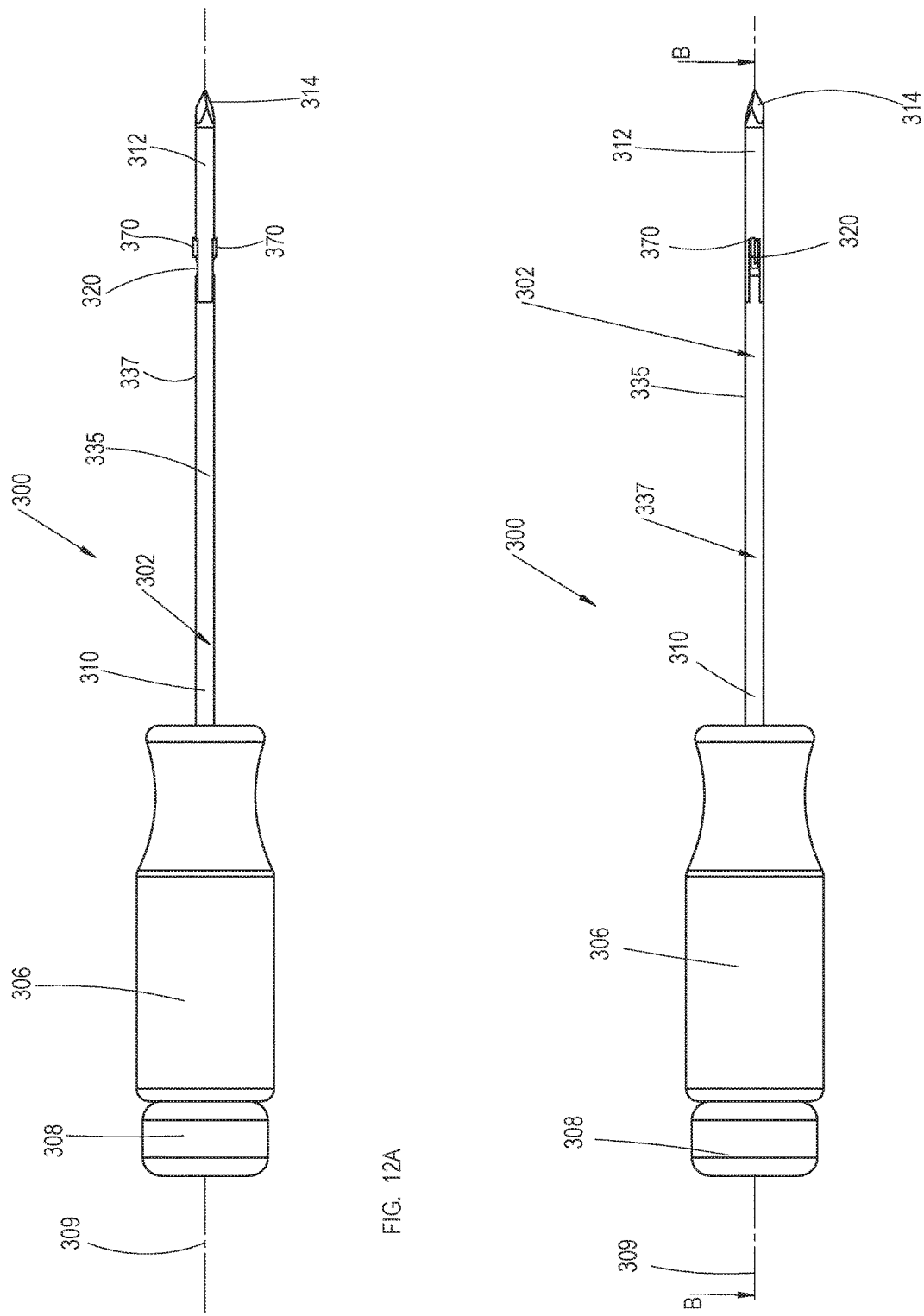
FIG. 12A illustrates two different simplified planar views, front and side views respectively, of the assembled bone material removal device of FIG. 7 in an open operative orientation.
Figure 12B:
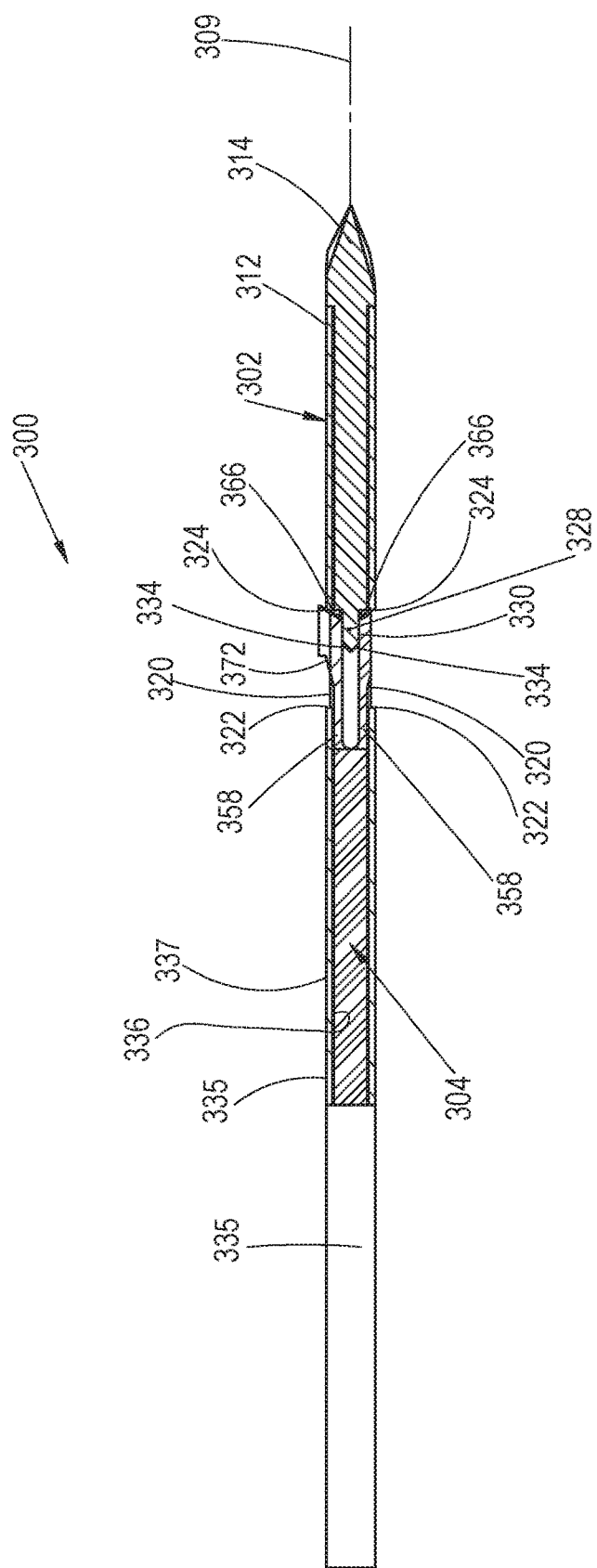
FIG. 12B is a simplified partial cross sectional view illustration of the assembled bone material removal device of FIG. 7 in the open operative orientation, section being taken along lines B-B in FIG. 12A.
Figure 12C:
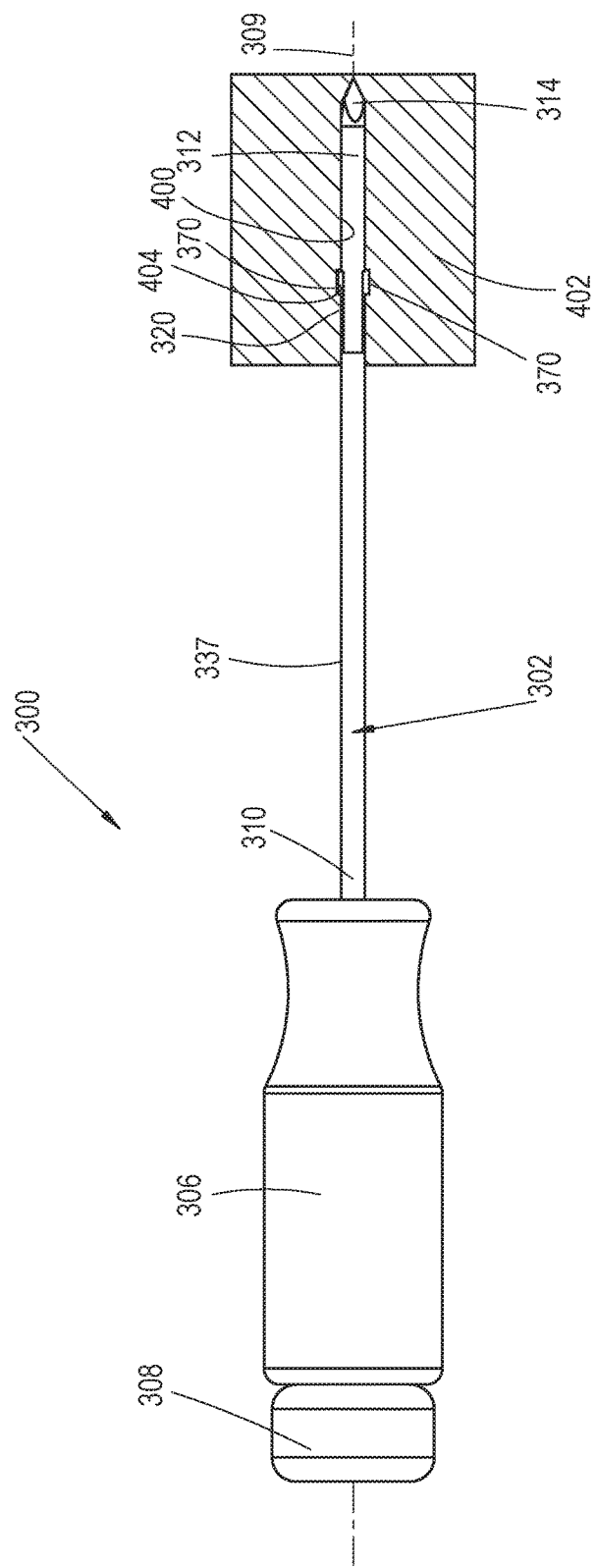
FIG. 12C is a simplified side view of the assembled bone material removal device in an open operative orientation shown within the bone of a patient.

Reference is now made to FIG. 12A, which illustrates two different simplified planar views, front and side views respectively, of the assembled bone material removal device 300 of FIG. 7 in a fully open operative orientation and to FIG. 12B, which is a simplified partial cross sectional view illustration of the assembled bone material removal device 300 of FIG. 7 in the fully open operative orientation, section being taken along lines B-B in FIG. 12A. Reference is additionally made to FIG. 12C, which is a simplified side view of the assembled bone material removal device 300 in a fully open operative orientation shown within the bone of a patient and to FIG. 12D, which is an enlargement of FIG. 12C, illustrating the assembled bone material removal device 300 in a fully open operative orientation shown within the bone of a patient.

It is seen in FIGS. 12A-12D that bore widening element 304 remains inserted into the drilling element 302, such that they are mutually arranged along longitudinal axis 309.

It is a particular feature of an embodiment of the present invention that the bore widening portion 304 is fully axially displaced with respect to drilling element 302.

It is particularly seen at this stage that pushing element 308 is now fully inserted into the handle 306, such that its distal end (not shown) engages proximally facing surface 356 of recess 354 of bore widening element 304 and thus axially displaces bore widening element 304 distally to be positioned at a distal location, thus providing for open operative orientation of the bone material removal device 300 It is appreciated that alternatively and optionally instead of utilizing handle 306 and pushing element 308, a power tool can be used, selectively changing between a closed operative orientation and an open operative orientation of the bone material removal device 300 for example, by means of changing the direction of rotation of the power tool, without requiring manipulation of mechanical means, such as pushing element 308.

Distal displacement of bore widening element 304 may bring widened portions 364 of arms 358 of bore widening element 304 to slide axially longitudinally with respect to the openings 320 of drilling element 302, such that the distally facing preferably inwardly proximally tapered or inclined surfaces 366 of bore widening element 304 engage distally extending tapered or inclined surfaces 334 of protrusion 328 of the drilling element 302 and slide therealong This brings tapered or inclined surfaces 334 to enter longitudinal recess 360 formed between the arms 358 of bore widening element 304 geometrically interfere with the axial movement of bore widening element 304 arms 358 and provides for outward radial deflection of arms 358 of bore widening element 304. Arms 358 succumb to bending forces thereupon and are thereby spaced one from another by means of outward radial force exerted by the distally extending tapered or inclined surfaces 334 entering longitudinal recess 360 formed between the arms 358 of widening element bringing about radial displacement and extension of widened carving portions 368 through one or more openings 320, positioning carving portions 368 in a fully extended position and bone material removal device 300 in a fully open operative orientation.

In this open operative orientation depicted in FIGS. 12A-12D, distally facing preferably inwardly proximally tapered or inclined surface 366 may be located adjacent the proximally facing shoulders 324 defined by openings 320 of the drilling element 302 and widened carving portions 368 and carving edges 370 locked in a radially extended position by cylindrical portion 330 of protrusion 328. Cylindrical portion 330 of protrusion 328 thereby acts as a counter support to support carving portions 368 in the extended position, oppose centrally directed radial forces and prevent carving portions 368 from retracting into drilling element 302.

It is therefore a particular feature of an embodiment of the present invention that axial movement of bore widening element 304 relative to protrusion 328 elastically and radially extends one or more carving portions 368 of bore widening element 304 arm 358 to a radially extended position.

It is a particular feature of an embodiment of the present invention that in the open operative orientation of the bone material removal device 300, carving edges 370 of bore widening portion 304 extend radially outwardly from the outer surface 337 of drilling element 302 through one or more openings 320 operative to carve bone in walls of a bore and create an undercut in the bone. Thus, the drilling diameter formed by the carving edges 370 of the bore widening element 304 is substantially greater than the drilling diameter initially formed by drilling tip 314 of the drilling element 302.

Figure 12D:
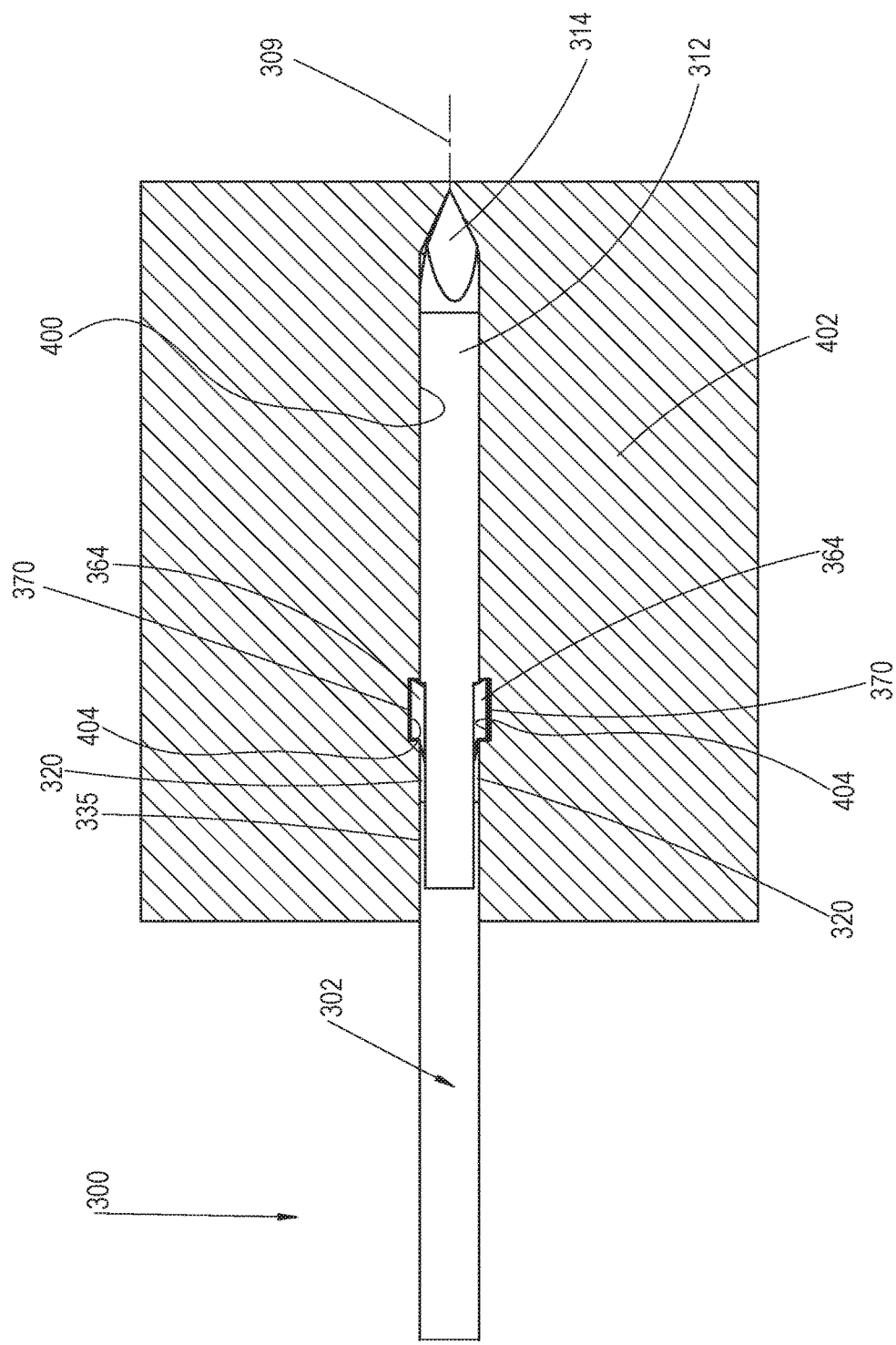
FIG. 12D is an enlargement of FIG. 12C, illustrating the assembled bone material removal device in an open operative orientation shown within the bone of a patient.

It is seen particularly in FIGS. 12C & 12D that an undercut 404 having a second diameter is formed over the initial bore 400 of a first diameter in the bone 402 of a patient, whereas the second diameter is substantially greater than the first diameter. The radius of the undercut can be for example in the range of 1.5 mm-2.5 mm, alternatively and optionally 1 mm-2 mm and alternatively and optionally 0.75 mm-1.25 mm.

Though carving edge 370 may be tapered to a point or inclined, it is a further particular feature of an embodiment of the present invention that 370 has a length and the length of the undercut 404 formed in the bone 402 of a patient is a function of the length of the carving edge 370 of the bore widening element 304.

It is appreciated that due to engagement between two tapered or inclined surfaces, namely distally facing optionally inwardly proximally tapered surface 366 of bore widening element 304 and distally extending tapered surfaces 334 of the drilling element, residual drilling material can be removed into recess 360, act as a lubricant and thus allow for smooth displacement of the widening element 304 with respect to the drilling element 302.

As shown in Figs. carving portion is optionally extended radially by bending forces exerted on a single surface of an arm of the widening element.

Referring once again to FIGS. 9A and 9B, in another embodiment bore widening element 304 depicted in FIGS. 9A and 9B may be in a stressed or loaded state inside drilling element 302, stressing bore widening element 304 arms 358 into an angle in respect to each other.

In the closed position of the example depicted in FIG. 10B, generally proximally inwardly tapered surface 372 of widened carving portion 368 are urged against openings 320 longitudinally extends from a distally facing shoulder 322, preventing widened carving portion 368 from extending radially. At this point in time and as shown in FIG. 10 an initial bore 400 of a first diameter can be formed within the bone 402 of a patient (FIGS. 10C and 10D).

At the point in time shown in FIG. 11, pushing element 308 has been partially advanced axially distally and is partially inserted into handle 306, such that its distal end engages bore widening element 304, axially displacing bore widening element 304 distally. Axial displacement of bore widening element 304 in respect to drilling element 302 brings proximally inwardly tapered surface 372 to gradually engage and slide over distally facing shoulder 322. Due to its elastic and shape memory qualities, bone material removal device 300 may tend to return to its original unstressed or resting state shape shown in FIGS. 9A and 9B once stress is relieved therefrom allowing bore widening element 304 arms 358 to extend outwardly radially through one or more openings 320.

It is seen in FIGS. 12A-12D that bore widening element 304 is fully axially displaced with respect to drilling element 302 and proximally inwardly tapered surface 372 is no longer in contact and limited by distally facing shoulder 322. This stage allows bore widening element 304 to fully return to its original unstressed or resting state shape shown in FIGS. 9A and 9B and bore widening element 304 arms 358 to fully extend outwardly radially through one or more openings 320.

Optionally, protrusion 328 may act as a counter support to support carving portions 368 in the extended position, oppose centrally directed radial forces and prevent carving portions 368 from retracting into drilling element 302.

It is therefore a particular feature of an embodiment of the present invention that axial movement of bore widening element 304 relative to protrusion 328 allows bore widening element 304 to fully return to its original unstressed or resting state shape bringing one or more carving edges of bore widening element 304 arm 358 to a radially extended position.

Referring back once again to FIG. 9A, widened carving portions 368 may include one carving edge or two or more carving edges 902 and 904 respectively, angled in respect to each other and joined at least at one end.

A first or main carving edge 902 may be operative to cut a main portion of a fragment of bone creating a first surface of the fragment and a second or auxiliary carving edge 904 may be operative to cut along a second adjoining surface of the fragment thus carving and detaching the fragment of bone.

When rotated in a direction depicted in FIG. 9A by an arrow designated reference numeral 950 a leading wall, defined by the direction of rotation and by main carving edge 902, auxiliary carving edge 904 and the angle therebetween, may define a rake angle 906 that provides a surface up and along which removed residual material (i.e., fragment of bone) may rise over an end relief or clearance curved surface 921 (broken line arrow 952) or along distally facing inwardly proximally tapered surface 366 to be collected into recess 360 (broken line arrow 954). Additionally, due to engagement between two tapered or inclined surfaces, namely distally facing inwardly proximally tapered surface 366 of the widening element and distally extending tapered surfaces 334 of the drilling element, residual drilling material can infiltrate recess 360, act as a lubricant and thus allow for smooth displacement of the widening element 304 with respect to the drilling element 302.

Figure 13A:
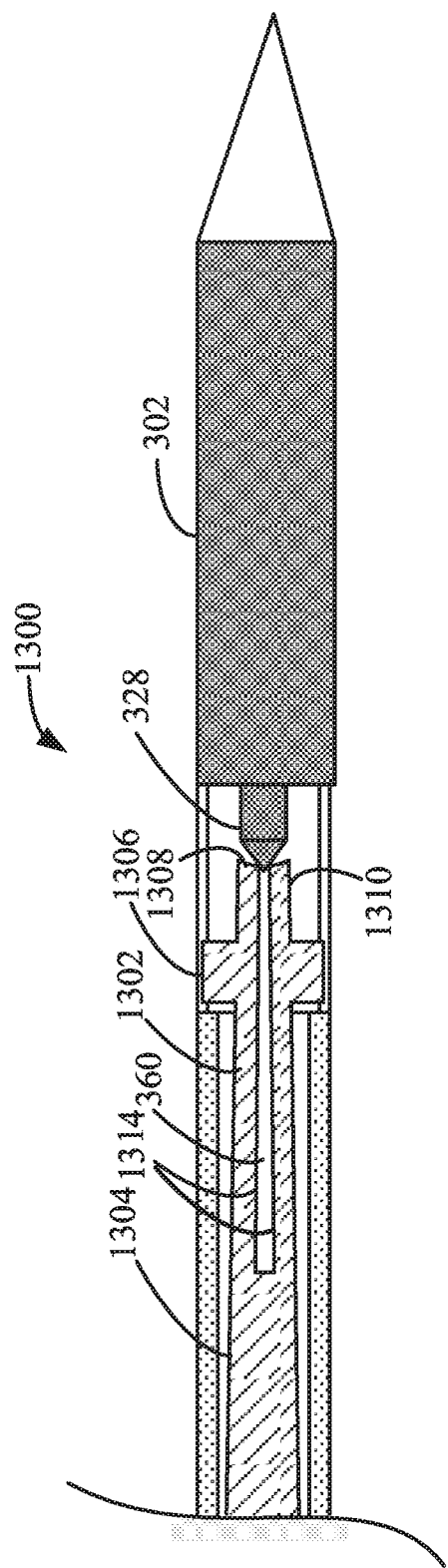
FIGS. 13A and 13B are cross section view simplified illustrations of additional embodiments of a bone material removal device.
Figure 13B:
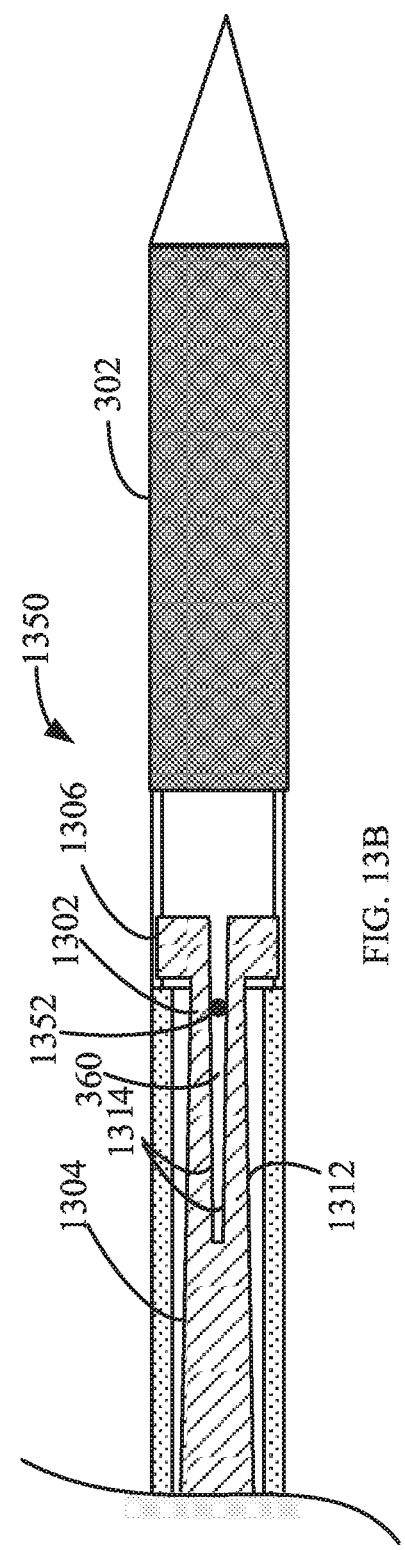

Reference is now made to FIGS. 13A and 13B, which are cross section view simplified illustrations of additional embodiments of a bone material removal device. FIG. 13A depicts an embodiment of a bone material removal device 1300 similar to the embodiment of FIG. 7, differing from the embodiment of FIG. 7 in that a non-carving end-portion 1310 of one or more arms 1302 of bore widening element 1304 extends distally beyond one or more carving portions 1306 and bordered proximally thereby terminating at inwardly proximally tapered or inclined surface 1308 of arms 1302.

Axial movement of bore widening element 1304 in respect to drilling element 302 brings inwardly proximally tapered or inclined surface 1308 of non-carving end-portion 1310 of arms 1302 to engage protrusion 328 that geometrically interferes with the axial movement of bore widening element 1304 and bends arms 1302 deflecting the arm bringing carving portion 1306 to travel and extend radially beyond a surface of the cannula and carve bone from a wall of a bore.

Alternately and optionally and as shown in FIG. 13B, an embodiment of a bone material removal device 1350 similar to the embodiment of FIG. 7, differing from the embodiment of FIG. 7 in that recess 360 is narrow proximately and widens distally bordered and defined by centrally facing surfaces 1314 of arms 1302 and a fixed protrusion 1352 is disposed abutting centrally facing surfaces 1314 and/or within a distal portion of recess 360 between two or more centrally facing surfaces 1314 of arms 1312. One or more non-carving proximal portions 1312 of arms 1302 extend from arms 1302 origin at the proximal border of recess 360 to a carving portion 1306 and distally bordered thereby. Axial movement of bore widening element 1304 brings one or more surfaces of non-carving proximal portions 1312 of arms 1302 defining recess 360 to be urged against protrusion 1352 that geometrically interferes with the axial movement of bore widening element 1304 and bends arms 1302 and deflecting the arm bringing carving portion 1306 to travel and extend radially beyond a surface of the cannula and carve bone from a wall of a bore.

As shown in FIGS. 10B, 11, 12B, 13A and 13B, carving portion 364/1306 is extended radially by bending forces exerted on a single surface of one or more arms 358/1302 of widening element 304/1304 respectively. Additionally, in some embodiments, when one or more arms 358/1302 are fully deflected and one or more carving portions 364/1306 are fully extended radially, one or more arms 358/1302 is generally parallel to the longitudinal axis of the device and carving portions 364/1306 supported by a counter support such as, for example, protrusion 328.

As depicted in FIGS. 14A and 14B, which are cross section view simplified illustrations of an embodiment of a bone material removal device 1400, a bore widening element 1402 including one or more carving portions 1404 may be limited to movement in a radial direction only and a pusher rod 1426 may be urged to move axially to engage the bore widening element actuating bore widening element 1402 that travels in a purely radial direction and bringing carving portion 1404 to travel and extend radially beyond surface 1406 of bone material removal device 1400.

As shown in FIG. 14A, bone material removal device 1400 may include a lumen 1428 that communicates with the atmosphere via an opening 1408 in a wall 1410 thereof. A distal margin 1412 of opening 1408 may be located at a predetermined distance proximally from a bone drilling tip 1414, opening 1408 extending longitudinally and proximally therefrom. Longitudinal bore widening element 1402 may include a bone carving portion 1404 that may be generally longitudinally widened defining an outer carving edge 1416 or several carving edges 1416. Bone carving portion 1404 may also define a radially positioned curved surface 1418 bordered at one side thereof by carving edge 1416 and forming an end relief or clearance curve that prevents the rubbing of carving portion 1404 against the bone, reducing the amount of force (e.g., torque) required for operation of bore widening device 1400.

Longitudinal bore widening element 1402 may be resiliently attached to wall 1410 of bore widening device 1400 by a resilient attachment that exerts constant tension in a radially inward direction, resisting outward radial extension of bore widening element 1402 such that at rest bone carving portion 1414 is at least partially retracted into a lumen 1420 of bone material removal device 1400 disposed within margins of opening 1408 and not protruding therefrom.

One or more elongated slot-like cutouts 1422 may be cut through the width of element 1402 the length of the cutouts oriented radially from the longitudinal axis of bone material removal device 1400. Movement of longitudinal bore widening element 1402 may be limited in a radial direction only by a radial-direction-guiding mechanism that includes one or more pins 1424 fixed to wall 1410 and protruding radially inward, optionally perpendicular to and through cutouts 1422. Bore widening element 1402 may also include an inclined surface 1424 along a border thereof or protruding from a surface of element 1402.

Bone material removal device 1400 may also include a pusher rod 1426 that moves axially within a lumen 1428 of bone material removal device 1400. Optionally, a tip 1430 of pusher rod 1426 may be inclined.

In operation, pusher rod 1426 may move axially and tip 1430 engages and slides along inclined surface 1424 exerting an outwardly radially directed force acting against and overcoming radially inward tension effected by the resilient attachment of bore widening element 1402 to wall 1410, actuating bore widening element 1402 that travels in a purely radial direction limited by the radial-direction guiding mechanism and brings bone carving portion 1404 to protrude circumferentially through opening 1408 into a fully extended bone carving position shown in FIG. 14B.

Retraction of pusher rod 1426 diminishes the outwardly radially directed force exerted upon inclined surface 1424 against the tension effected by the resilient attachment of bore widening element 1402 to wall 1410 that now, with no outwardly radially directed counter force returns to its resting state radially centrally urging bore widening element 1402 back into a retracted position inside lumen 1428 and bone carving portion 1414 disposed within margins of opening 1408 and not protruding therefrom.

Carving portion 1404 may be similar in structure to widened carving portion 368 also including a first carving edge 902, a second carving edge 904 and the angle therebetween that may define a rake angle 906 that provides a surface up and along which removed residual material (i.e., fragment of bone) may rise over an end relief or clearance curved surface 921 to be collected into bone material removal device 1400.

First carving edge 902 may cut a main portion of a fragment of bone creating a first surface of the fragment and second carving edge 904 may cut along a second adjoining surface of the fragment thus carving and detaching the fragment of bone.

It is expected that during the life of a patent maturing from this application many relevant bone removal mechanisms will be developed; the scope of the term "bone carving" is intended to include all such new technologies a priori.

As used herein with reference to quantity or value, the term "about" means "within ±15% of".

The terms "comprises", "comprising", "includes", "including", "has", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular forms "a", "an" and "the" include plural references unless the context clearly dictates otherwise. For example, the term "a compound" or "at least one compound" may include a plurality of compounds, including mixtures thereof.

Throughout this application, embodiments of this invention may be presented with reference to a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as "from 1 to 6" should be considered to have specifically disclosed subranges such as "from 1 to 3", "from 1 to 4", "from 1 to 5", "from 2 to 4", "from 2 to 6", "from 3 to 6", etc.; as well as individual numbers within that range, for example, 1, 2, 3, 4, 5, and 6. This applies regardless of the breadth of the range.

Whenever a numerical range is indicated herein (for example "10-15", "10 to 15", or any pair of numbers linked by these another such range indication), it is meant to include any number (fractional or integral) within the indicated range limits, including the range limits, unless the context clearly dictates otherwise. The phrases "range/ranging/ranges between" a first indicate number and a second indicate number and "range/ranging/ranges from" a first indicate number "to", "up to", "until" or "through" (or another such range-indicating term) a second indicate number are used herein interchangeably and are meant to include the first and second indicated numbers and all the fractional and integral numbers therebetween.

Unless otherwise indicated, numbers used herein and any number ranges based thereon are approximations within the accuracy of reasonable measurement and rounding errors as understood by persons skilled in the art.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A device for removal of bone from a wall of a bore comprising:
    a cannula having a hollow portion and a long axis;
    an interference element located inside said hollow portion of the cannula, said interference element being elongate and extending in an axial direction;
    a bore widening element configured for axial movement relative to said interference element along said long axis inside said hollow portion of said cannula; and a bone carving portion coupled to said bore widening element; said bone carving portion including:

a cutting edge directed radially away from said long axis and a clearance surface bordered by said cutting edge; said clearance surface directed radially away from said long axis and curving circumferentially around said long axis;

wherein said axial movement causes said interference element to engage said bore widening element and exert onto said bore widening element a force radially outward with respect to said long axis; said radially outward force causing said cutting edge to extend radially away from said long axis from a retracted position to an extended position in which said cutting edge is extended radially away from said long axis beyond an outer surface of the cannula; and wherein an angle of said clearance surface relative to said long axis in said retracted position is substantially the same as an angle of said clearance surface relative to said long axis in said extended position.

2. A device according to claim 1, wherein the bore widening element is a single elastic member.

3. A device according to claim 1, wherein the bore widening element includes an arm oriented along said long axis having a free end facing said interference element and wherein the carving portion is coupled to said free end.

4. A device according to claim 1, wherein said carving portion comprises first and second carving edges angled in respect to one another and joined at least at one end and wherein the first carving edge, the second carving edge and the angle therebetween define a rake angle that provides a surface on said carving portion up and along which removed residual material rises and is collected into the hollow portion of the cannula.

5. A device according to claim 1, wherein the bore widening element includes a first arm and a second arm separated by a longitudinal recess extending substantially parallel to said long axis, said recess having a closed end and an open end facing said interference element and said carving portion coupled to said first arm towards the open end thereof.

6. A device according to claim 3, wherein said carving portion is configured to extend radially by bending forces exerted on a single surface of said arm of the widening element.

7. A device according to claim 1, wherein the cannula also comprises at least one through opening in a wall of said hollow portion of the cannula and wherein at least a portion of the bone carving portion extends radially through said at least one opening in said extended position.

8. A device according to claim 7, wherein the carving portion comprises at least one surface which tapers proximally inwardly relative to said long axis and the bore widening element is housed in a stressed state within the cannula and wherein the axial displacement is configured to urge the at least one surface against and over a distally facing shoulder of the at least one through opening in said cannula to bring about said extension of said carving edge from said retracted position to said extended position.

9. A device according to claim 8, wherein the radial extension of at least one carving portion is effected by the tendency of the stressed bore widening element to return to its original resting state.

10. A device according to claim 1, wherein the interference element includes a counter support to support the carving portion in the extended position positioned radially inward of said carving portion.

11. A device according to claim 1, wherein the interference element includes a counter support to oppose centrally directed inward radial forces by means of exerting an outward radial force on the carving portion and preventing the carving portion from retraction back into the cannula.

12. A device according to claim 3, wherein the arm, when fully deflected radially outwardly, is generally parallel to the long axis of the device and a blade of said bone carving portion supported by a counter support of said interference element.

13. A device according to claim 2, wherein the single elastic member is moveably housed in the cannula.

14. A device according to claim 1, wherein said cannula includes a forward bore drilling tip on a distal end thereof.

15. A device according to claim 2, wherein the device comprises a cylindrical portion located at the distal end of the cannula, the diameter of the inner circumference of the cylindrical portion is substantially equal to the outer diameter of a portion of the single elastic member that is thickest in a radial direction and supports axial and rotational movement and restrains radial movement of the single elastic member.

16. A device according to claim 3, further including:

a forward tip on a distal end of said cannula and wherein the interference element extends proximally between the forward tip and the bore widening element and wherein the free end of said arm faces distally and said free end also includes a surface facing said long axis and inclined to face distally at a distal aspect thereof and wherein the axial movement causes the inclined surface to engage the interference element that geometrically interferes with the axial movement of the bore widening element and bends the arm and deflects the carving portion radially outward from said long axis.

17. A device according to claim 12, wherein said support comprises a protrusion.

18. The device of claim 1, wherein a geometry of said cutting edge and said clearance surface in said extended position is substantially the same as a geometry of said cutting edge and said clearance surface in said retracted position.

19. The device of claim 1, wherein said clearance surface curves circumferentially around said long axis in said retracted position and in said extended position.

20. The device according to claim 1, wherein said interference element is coaxial with said long axis.

21. The device according to claim 1, wherein said interference element is elongate and extends along a length of said cannula.

22. The device according to claim 1, wherein said bore widening element is housed in a stressed state within said cannula when in said retracted position.

23. The device according to claim 1, wherein said device includes an elongate arm having said bore widening element; and wherein said axial movement causes said interference element to engage said elongate arm having said bore widening element and to exert onto said elongate arm having said bore widening element a bending force radially outward with respect to said long axis, said radially outward bending force bending said elongate arm and causing said cutting edge to extend radially away from said long axis from said retracted position to said extended position.

24. The device according to claim 1, wherein said device comprises a plurality of arms, at least one said arm having said bore widening element; and wherein said axial movement causes said interference element to engage said arms, to enter into a longitudinal recess formed between said arms, and to exert onto said arms a bending force radially outward with respect to said long axis, said radially outward bending force bending said arms and causing said cutting edge to extend radially away from said long axis from said retracted position to said extended position.

25. The device according to claim 1, including a living hinge wherein said axial movement causes said interference element to engage said bore widening element and exert onto said bore widening element the force radially outward with respect to said long axis; said radially outward force causing said cutting edge to extend radially away from said long axis from the retracted position to the extended position.

26. The device according to claim 1, wherein said device includes an elongate arm having said bore widening element; and wherein said axial movement causes said interference element to engage said elongate arm having said bore widening element and to exert onto said elongate arm having said bore widening element a deflecting force radially outward with respect to said long axis; said radially outward deflecting force deflecting said elongate arm and causing said cutting edge to extend radially away from said long axis from the retracted position to the extended position in which said cutting edge is parallel to said long axis.

27. The device according to claim 1, wherein an angle of said cutting edge relative to said long axis in said extended position is the same as an angle of said cutting edge relative to said long axis in said retracted position.

28. The device according to claim 1, wherein said axial movement of said bore widening element is along said long axis and past said interference element.

29. A device for removal of bone from a wall of a bore comprising:

a cannula having a hollow portion and a long axis;

an interference element located inside said hollow portion of the cannula, said interference element being elongate and extending in an axial direction;

a bore widening element configured for axial movement relative to said interference element along said long axis inside said hollow portion of said cannula; and a bone carving portion coupled to said bore widening element; said bone carving portion including a cutting edge directed radially away from said long axis;

wherein said axial movement causes said interference element to engage said bore widening element and exert onto said bore widening element a force radially outward with respect to said long axis; said radially outward force causing said cutting edge to extend radially away from said long axis from a retracted position to an extended position in which said cutting edge is extended radially away from said long axis beyond an outer surface of the cannula; and wherein an angle of said bore widening element relative to said long axis in said extended position is the same as an angle of said bore widening element relative to said long axis in said retracted position.

* * * * *